United States Patent
Samples et al.

(10) Patent No.: US 11,948,114 B2
(45) Date of Patent: Apr. 2, 2024

(54) AUDIT-BASED COMPLIANCE DETECTION FOR HEALTHCARE SITES

(71) Applicant: Innovation Associates Inc., Johnson City, NY (US)

(72) Inventors: Phil Samples, Willard, MO (US); Rebecca Keefe, Binghampton, NY (US); Keith Redmore, Binghampton, NY (US); Alecia Lashier, Johnson City, NY (US)

(73) Assignee: Innovation Associates Inc., Johnson City, NY (US)

( * ) Notice: Subject to any disclaimer, the term of this patent is extended or adjusted under 35 U.S.C. 154(b) by 338 days.

(21) Appl. No.: 16/896,901

(22) Filed: Jun. 9, 2020

(65) Prior Publication Data
US 2021/0383292 A1      Dec. 9, 2021

(51) Int. Cl.
*G06Q 10/0635* (2023.01)
*G06Q 30/018* (2023.01)
*G06Q 30/0282* (2023.01)
*G06Q 40/08* (2012.01)
*G06Q 50/26* (2012.01)
*G16H 40/20* (2018.01)

(52) U.S. Cl.
CPC ....... *G06Q 10/0635* (2013.01); *G06Q 30/018* (2013.01); *G06Q 30/0282* (2013.01); *G16H 40/20* (2018.01); *G06Q 40/08* (2013.01); *G06Q 50/26* (2013.01)

(58) Field of Classification Search
None
See application file for complete search history.

(56) References Cited

U.S. PATENT DOCUMENTS

| | | | |
|---|---|---|---|
| 8,484,066 B2* | 7/2013 | Miller | G06Q 10/08 726/23 |
| 8,639,527 B2 | 1/2014 | Rensvold et al. | |
| 9,639,820 B2 | 5/2017 | Singh et al. | |
| 9,721,296 B1* | 8/2017 | Chrapko | G06Q 30/018 |

(Continued)

FOREIGN PATENT DOCUMENTS

| CN | 110472756 A | * 11/2019 |
|---|---|---|
| CN | 110717082 | 1/2020 |
| CN | 110853723 | 2/2020 |

OTHER PUBLICATIONS

Merrit et al. "Overview of risk assessments and workplans" 2020 (retrieved from https://assets.hcca-info.org/Portals/0/PDFs/Resources/Conference_Handouts/Regional_Conference/2020/Ann_Arbor/830-930_Merritt_Constantino.pdf) (Year: 2020).*

*Primary Examiner* — Sujay Koneru
(74) *Attorney, Agent, or Firm* — K&L Gates LLP

(57) ABSTRACT

Methods and systems for improved collection and evaluation of audit responses for healthcare sites are provided. In one embodiment, a method is provided that includes receiving responses associated with an audit of a healthcare site. A deficiency score and a total score may be calculated based on the responses. The deficiency scores may be calculated based on a quantity of responses indicating a deficient status and/or an improvement required status. The total score may be calculated based on a total quantity of the responses and a quantity of the responses that indicate an inapplicable status. The risk score may then be calculated based on the deficiency score.

20 Claims, 9 Drawing Sheets

(56) References Cited

U.S. PATENT DOCUMENTS

| | | | |
|---|---|---|---|
| 10,152,608 B2* | 12/2018 | Kulkarni | G16Z 99/00 |
| 2003/0167187 A1* | 9/2003 | Bua | G16H 40/20 |
| | | | 702/182 |
| 2005/0144480 A1* | 6/2005 | Kim | H04L 63/1433 |
| | | | 726/4 |
| 2006/0282276 A1* | 12/2006 | Venzon | G06Q 50/18 |
| | | | 705/317 |
| 2007/0239495 A1* | 10/2007 | Osborn | G06Q 10/0639 |
| | | | 714/E11.207 |
| 2008/0154637 A1 | 6/2008 | Capelli et al. | |
| 2011/0202556 A1* | 8/2011 | Fernandez | G16H 10/60 |
| | | | 707/769 |
| 2012/0053982 A1* | 3/2012 | Treacey | G06Q 10/0635 |
| | | | 705/7.28 |
| 2012/0072260 A1* | 3/2012 | Graham | G06F 16/335 |
| | | | 705/7.32 |
| 2012/0303378 A1* | 11/2012 | Lieberman | G06Q 40/08 |
| | | | 705/2 |
| 2012/0330852 A1* | 12/2012 | Kochevar | G06Q 10/20 |
| | | | 705/317 |
| 2013/0006665 A1* | 1/2013 | Fernandez | G16H 50/70 |
| | | | 705/3 |
| 2013/0246291 A1* | 9/2013 | Dick | G06Q 10/00 |
| | | | 705/317 |
| 2013/0262357 A1* | 10/2013 | Amarasingham | G16H 50/70 |
| | | | 706/21 |
| 2013/0297346 A1* | 11/2013 | Kulkarni | G16H 10/60 |
| | | | 705/3 |
| 2013/0304485 A1* | 11/2013 | Khan | G16H 40/67 |
| | | | 705/2 |
| 2013/0311387 A1* | 11/2013 | Schmerler | G06Q 30/018 |
| | | | 705/317 |
| 2013/0317870 A1* | 11/2013 | Franco | G06Q 10/06 |
| | | | 705/7.11 |
| 2014/0006296 A1* | 1/2014 | Hughes | A61F 13/4963 |
| | | | 705/317 |
| 2014/0026131 A1* | 1/2014 | Ravi | G06F 8/60 |
| | | | 717/177 |
| 2014/0081652 A1 | 3/2014 | Klindworth | |
| 2014/0164039 A1* | 6/2014 | Mitti | G06Q 10/06311 |
| | | | 705/7.14 |
| 2014/0220540 A1* | 8/2014 | Burgin | G09B 7/07 |
| | | | 434/362 |
| 2014/0229228 A1* | 8/2014 | Rose | G06Q 10/06 |
| | | | 705/7.28 |
| 2014/0257047 A1* | 9/2014 | Sillay | H04L 63/10 |
| | | | 600/595 |
| 2014/0278730 A1* | 9/2014 | Muhart | G06Q 10/0635 |
| | | | 705/7.28 |
| 2014/0279601 A1* | 9/2014 | McClelland | G06Q 30/018 |
| | | | 705/317 |
| 2014/0279641 A1 | 9/2014 | Singh et al. | |
| 2014/0337054 A1* | 11/2014 | Kulkarni | G16H 10/60 |
| | | | 705/3 |
| 2015/0213225 A1* | 7/2015 | Amarasingham | G16H 50/30 |
| | | | 705/2 |
| 2015/0347705 A1 | 12/2015 | Simon et al. | |
| 2017/0206336 A1 | 7/2017 | Lee et al. | |
| 2017/0262609 A1* | 9/2017 | Perlroth | G16H 10/60 |
| 2018/0182475 A1* | 6/2018 | Cossler | G16H 50/50 |
| 2018/0367561 A1* | 12/2018 | Givental | G06F 21/552 |
| 2019/0050780 A1* | 2/2019 | Koch | G06Q 10/06393 |
| 2019/0066849 A1* | 2/2019 | Lawrence | G06F 40/205 |
| 2019/0287675 A1* | 9/2019 | Ghosh | G16H 10/20 |
| 2019/0348171 A1* | 11/2019 | Nachmany | G16H 40/20 |
| 2020/0253820 A1* | 8/2020 | Walker | A61B 5/0836 |
| 2020/0273046 A1* | 8/2020 | Biswas | G06N 3/08 |
| 2020/0302775 A1* | 9/2020 | Liu | G06K 7/10366 |
| 2020/0380436 A1* | 12/2020 | Bonomo | G06Q 10/1091 |
| 2021/0035692 A1* | 2/2021 | Buslovich | G16H 10/20 |
| 2021/0381861 A1* | 12/2021 | Brown | G05D 23/1917 |
| 2022/0035896 A1* | 2/2022 | Brannon | G06F 11/3438 |
| 2022/0238222 A1* | 7/2022 | Neuberg | G16H 50/20 |

\* cited by examiner

Audit Database 200

- Audit 204 — Type: Self Audit
- Audit 206 — Type: Self Audit
- Audit 208 — Type: Self Audit
- Audit 210 — Type: Self Audit
- Audit 212 — Type: On-Site
- Audit 214 — Type: On-Site
- Audit 216 — Type: On-Site
- Audit 218 — Type: Regional
- Audit 220 — Type: Off-Site

FIG. 2

AUDIT-BASED COMPLIANCE DETECTION FOR HEALTHCARE SITES

BACKGROUND

To ensure adequate levels of patient care, healthcare providers may be required to comply with multiple policies. For example, healthcare providers may be required to comply with policies established by governments (e.g., federal governments, state governments, local governments), insurance providers, state boards of health, company boards (e.g., boards of directors for the healthcare providers), management (e.g., business management for the healthcare providers), and customers. If a healthcare provider, or a healthcare site provided by the healthcare provider, fails to comply with one or more of these policies, patient care may suffer and/or the healthcare provider may be financially penalized.

SUMMARY

The present disclosure presents new and innovative systems and methods for creating and evaluating audit responses for healthcare sites. In a first aspect, a method is provided that includes (a) receiving a plurality of responses associated with an audit of a healthcare site and (b) calculating a deficiency score for the healthcare site based on a first quantity of a subset of the plurality of responses indicating a deficient status for the healthcare site and a second quantity of a subset of the plurality of responses indicating an improvement required status for the healthcare site. The method may also include (c) calculating a total score for the healthcare site based on a third quantity of the plurality of responses and a fourth quantity of a subset of the plurality of responses indicating an inapplicable status. The method may further include (d) calculating a risk score for the healthcare site based on the deficiency score and the total score.

In a second aspect according to the first aspect, the deficiency score is calculated by applying a first weight to the first quantity and a second weight to the second quantity.

In a third aspect according to the second aspect, the first weight is greater than the second weight.

In a fourth aspect according to the third aspect, the first weight is at least two times larger than the second weight.

In a fifth aspect according to any of the first through fourth aspects, the total score is calculated by subtracting the fourth quantity from the third quantity.

In a sixth aspect according to any of the first through fifth aspects, the risk score is calculated by dividing the deficiency score by the total score.

In a seventh aspect according to the sixth aspect, the risk score is calculated by subtracting an adjustment value from each of the deficiency score and the total score prior to dividing.

In an eighth aspect according to the seventh aspect, the adjustment value is determined based on the total score and a configurable value.

In a ninth aspect according to any of the first through eighth aspects, at least one of (i) the first quantity is calculated by summing risk values associated with the subset of the plurality of responses indicating the deficient status, (ii) the second quantity is calculated by summing risk values associated with the subset of the plurality of responses indicating the improvement required status, (iii) the third quantity is calculated by summing risk values associated with the plurality of responses, and (iv) the fourth quantity is calculated by summing risk values associated with the subset of the plurality of responses indicating the inapplicable status.

In a tenth aspect according to any of the first through ninth aspects, the method further includes combining the risk score with a plurality of additional risk scores associated with additional healthcare sites to generate an aggregate risk score.

In an eleventh aspect according to any of the first through tenth aspects, the method further includes combining the risk score with at least one previous risk score associated with the healthcare site to generate a risk trend measurement for the healthcare site.

In a twelfth aspect according to any of the first through eleventh aspects, (a) includes receiving a first plurality of responses associated with a regional audit of the healthcare site and a second plurality of responses associated with an on-site audit, and wherein (b)-(d) are performed twice to calculate a first risk score based on the first plurality of responses and a second risk score based on the second plurality of responses.

In a thirteenth aspect according to the twelfth aspect, the method further includes combining the first risk score and the second risk score to generate an overall risk score for the healthcare site.

In a fourteenth aspect according to any of the first through thirteenth aspects, the deficient status includes any response indicating that a condition corresponding to the response does not comply with requirements for the condition.

In a fifteenth aspect according to any of the first through fourteenth aspects, the improvement required status includes any response indicating that a condition corresponding to the response currently complies with requirements for the condition, but required correction before achieving compliance.

In a sixteenth aspect, a system is provided that includes a memory and a processor. The memory may store instructions which, when executed by the processor, cause the processor to (a) receive a plurality of responses associated with an audit of a healthcare site and (b) calculate a deficiency score for the healthcare site based on a first quantity of a subset of the plurality of responses indicating a deficient status for the healthcare site and a second quantity of a subset of the plurality of responses indicating an improvement required status for the healthcare site. The memory may also store instructions which, when executed by the processor, cause the processor to (c) calculate a total score for the healthcare site based on a third quantity of the plurality of responses and a fourth quantity of a subset of the plurality of responses indicating an inapplicable status. The memory may store further instructions which, when executed by the processor, cause the processor to (d) calculate a risk score for the healthcare site based on the deficiency score and the total score.

In a seventeenth aspect according to the sixteenth aspect, the deficiency score is calculated by performing at least one of (i) applying a first weight to the first quantity and a second weight to the second quantity, (ii) subtracting the fourth quantity from the third quantity, and (iii) dividing the deficiency score by the total score.

In an eighteenth aspect according to any of the sixteenth and seventeenth aspects, wherein at least one of (i) the first quantity is calculated by summing risk values associated with the subset of the plurality of responses indicating the deficient status, (ii) the second quantity is calculated by summing risk values associated with the subset of the plurality of responses indicating the improvement required status, (iii) the third quantity is calculated by summing risk values associated with the plurality of responses, and (iv) the fourth quantity is calculated by summing risk values associated with the subset of the plurality of responses indicating the inapplicable status.

In a nineteenth aspect according to any of the sixteenth through eighteenth aspects, the memory stores further instructions which, when executed by the processor, cause the processor to perform at least one of (i) combining the risk score with a plurality of additional risk scores associated with additional healthcare sites to generate an aggregate risk score and (ii) combining the risk score with at least one previous risk score associated with the healthcare site to generate a risk trend measurement for the healthcare site.

In a twentieth aspect according to any of the sixteenth through nineteenth aspects, the deficient status includes any response indicating that a condition corresponding to the response does not comply with requirements for the condition. The improvement required status may include any response indicating that a condition corresponding to the response currently complies with requirements for the condition, but required correction before achieving compliance.

The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the disclosed subject matter.

BRIEF DESCRIPTION OF THE FIGURES

FIG. 2 illustrates an audit database according to an exemplary embodiment of the present disclosure.

DETAILED DESCRIPTION OF EXAMPLE EMBODIMENTS

Figure 1:
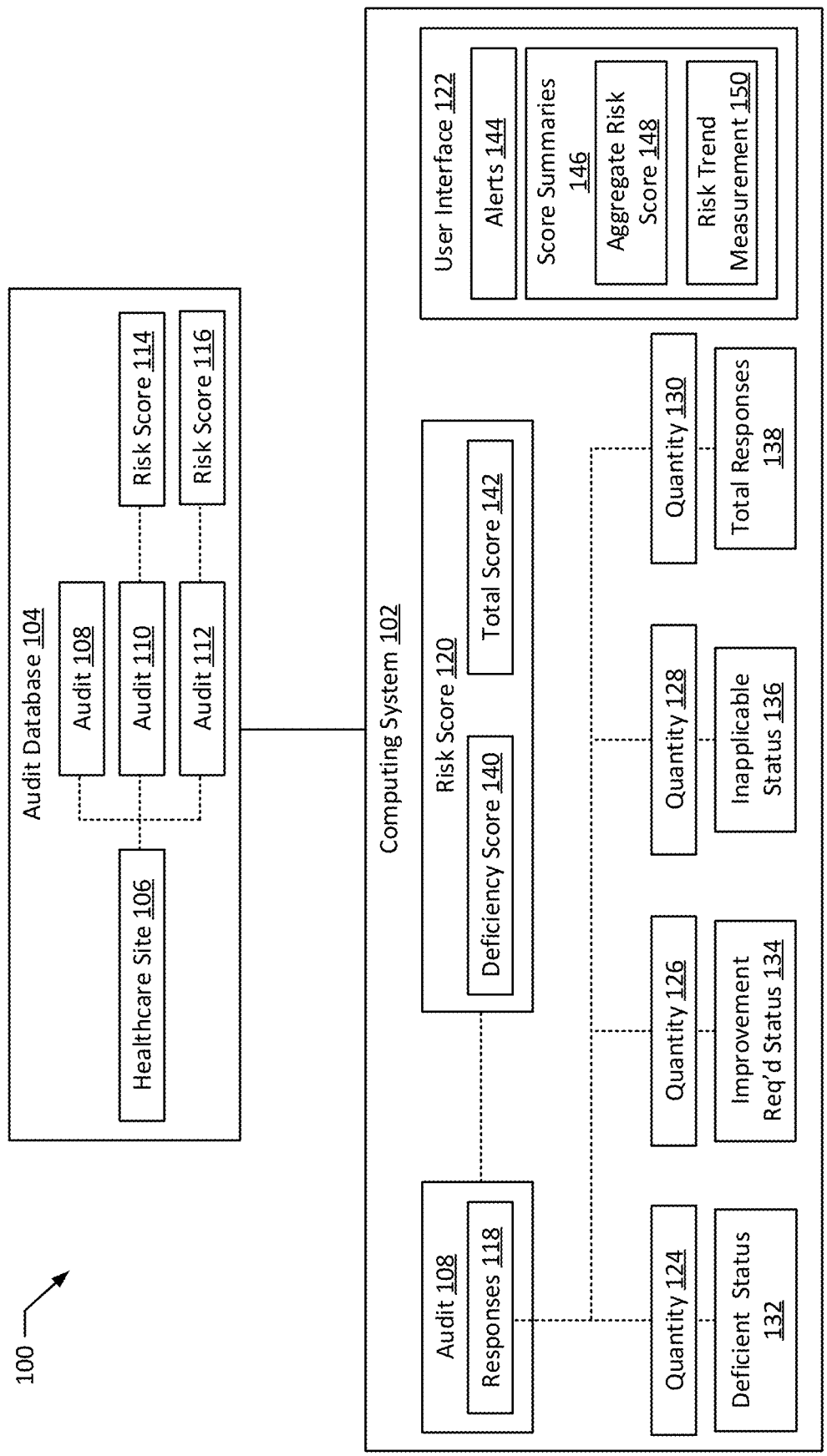
FIG. 1 illustrates a system according to an exemplary embodiment of the present disclosure.

To avoid negative outcomes from failing to comply with applicable policies, healthcare providers may establish systems to ensure company and employee compliance with healthcare policies. For example, healthcare providers may task one or more employees with performing audits that compare the behavior of the healthcare provider and its employees against one or more of the healthcare policies. For example, the audits may include one or more questions regarding particular provisions and/or requirements of a healthcare policy. Employees may assess healthcare provider behavior (e.g., current conditions of the healthcare provider, historical behavior of employees, current behaviors of employees, and the like) based on the question and may provide a response to the questions based on the healthcare provider behavior. For example, a question may ask whether current behavior complies with a particular requirement of a policy and the response may indicate either that the current behavior does comply with the requirement or that the current behavior does not comply with the particular requirement. As a specific example, the question may ask whether current prescription storage practices at the healthcare provider comply with a requirement that potentially dangerous medicines (e.g., controlled substances) be stored separate from other medicines. An employee completing the audit may locate one or more controlled substances, determine that the controlled substances are stored separate from other medicines, and provide a response to the audit indicating that the current behavior of the healthcare provider complies with the requirement.

In this way, audits may be performed on a systematic basis by many different employees, who may be distributed across multiple healthcare sites. Data from the audits (e.g., responses to questions of the audits) may be received. However, aggregation and analysis of this data is rendered cumbersome by existing technical implementations. In particular, different types of policies (e.g., information technology (IT) policies, medical storage policies, medical care policies, financial policies, accounting policies) are managed by different stakeholders and/or departments within a healthcare provider's business (e.g., an IT department, a security department, a medical care department, a financial department, an accounting department). Each stakeholder may be responsible for establishing, conducting, and analyzing audits for their corresponding policies. Accordingly, audit responses regarding the healthcare provider may be spread across multiple databases and/or computing systems implemented by the different stakeholders and/or departments. In particular, different employees may be required to access data within different computing systems regarding responses to audits for the various stakeholders. Furthermore, audit responses may be stored in different formats depending on the policy the audit is prepared for, the stakeholder or department that prepared the audit, and/or the employee who entered the responses to the audit. For example, certain audit responses may have specific, limited options (e.g., "compliant," "noncompliant"), other audit responses may have a range of available options (e.g., rating on a scale from 0-10), and still further audit responses may have free response options (e.g., text fields for entry by an employee completing the audit).

Because of the disparate nature in how audits are prepared and stored and/or the different formats in which responses may be entered, manual analysis of audit responses may be required to track policy compliance for multiple healthcare sites, to compare policy compliance for multiple healthcare sites, to monitor policy compliance over time within the healthcare provider, to determine policy compliance across different types of policies managed by different stakeholders within the healthcare provider, and the like. For example, a regional manager may be responsible for five different healthcare sites that each must comply with at least three different policies: a pharmaceutical storage policy, an employee safety policy, and a customer safety policy. Audits for these policies may be prepared by different departments within a healthcare provider. For example, an audit for the pharmaceutical storage policy may be prepared by a pharmaceutical department within the healthcare provider and audits for the employee safety policy and the customer safety policy may be prepared by a risk management department within the healthcare provider. In such instances, the audit for the pharmaceutical storage policy may be stored in a separate system (e.g., a separate database entry system, a separate personnel management system) from the audits for the employee safety policy and the customer safety policy. In such instances, to determine compliance for each of the five healthcare sites, the regional manager may be required to log into two separate computing systems and access three different audits for each healthcare site. This process is repetitive and cumbersome and further requires the regional manager to compile and analyze the data manually (e.g., using data analysis tools). In practice, of course, healthcare sites may have to comply with many more policies, requiring additional audits and/or additional audit responses. Accordingly, existing systems may in fact require even more cumbersome data analysis practices.

In such instances, the analysis results may be both slow to prepare and error-prone. Accordingly, management may be unaware of developing risk issues in particular healthcare sites for extended periods of time as employees prepare the analysis. Additionally, errors in the analysis may result in the failure to detect potential risks at particular healthcare sites and/or may result in unnecessary risk management practices at healthcare sites that do not require further adjustment or attention. Furthermore, where the analysis depends on employee input, such systems increase the risk of fraud, as employees may falsely indicate that particular healthcare sites (e.g., particular healthcare sites under the employees' responsibility) do not present an ongoing operating risk even when that is not the case. Accordingly, there exists a need to provide automatic, aggregated analysis of audit results for healthcare sites within a healthcare provider into a format that can be clearly understood and analyzed by healthcare provider stakeholders (e.g., management, boards, auditors, employees).

One solution to this problem is to compute risk scores for healthcare sites on an automated and consistent basis. In particular, audits may be collected from multiple sources within a healthcare provider and the collected audits may be analyzed to compute risk scores for corresponding healthcare sites. For example, risk scores may be calculated for healthcare sites based on individual audits corresponding to the healthcare sites. In particular, risk scores may be calculated based on a deficiency score and a total score. The deficiency score may be calculated to determine a number of questions and/or responses within an audit that indicate that the healthcare site did not comply with one or more policy requirements. For example, the deficiency score may be calculated to include responses identifying currently-deficient conditions of the healthcare site and/or previously-deficient conditions at the healthcare site. The total score may be calculated to determine a total number of policy requirements and/or questions from an audit applied to the healthcare sites. For example, the total score may be calculated based on a total number of responses in an audit and a number of responses indicating that questions do not apply to the healthcare site.

Performing an automated analysis in this way results in a risk score for the healthcare site which can be easily understood and compared to risk scores for other healthcare sites. Furthermore, the risk score is calculated to comprehensively incorporate different types of statuses in the responses, allowing the risk score to account for nuanced situations (e.g., where a previously non-compliant healthcare site is demonstrating improvement). Furthermore, the risk score calculation may incorporate risk values for each of the questions, allowing the score to prioritize questions and responses related to the biggest risks, thereby incorporating expert knowledge from various stakeholders, including individuals with risk management expertise. Furthermore, an automated analysis and calculation of the risk score may enable the automated presenting of alerts when it is determined that further intervention may be needed. Also, a calculated risk score may be compared with other risk scores over time to generate a historical risk measure for the healthcare site or may be combined with risk scores of other sites to generate an aggregate risk measure (e.g., for regional managers, directors, and the like responsible for multiple healthcare sites).

FIG. 1 illustrates a system 100 according to an exemplary embodiment of the present disclosure. The system 100 may be configured to receive and analyze audits to determine a risk level for healthcare sites. In particular, the system 100 may be configured to receive and store responses to audits regarding policies applicable to healthcare sites and to compute risk scores for the healthcare sites based on the responses to the audits.

The system 100 includes a computing system 102 and an audit database 104. The audit database 104 may be configured to receive and store multiple audits 108, 110, 112. In particular, the audits 108, 110, 112 may correspond to a particular healthcare site 106. For example, the healthcare site 106 may include one or more of a hospital, a department within a hospital, a floor of a hospital, a doctor's office, a pharmacy (a retail pharmacy, a mail order pharmacy), a pharmaceutical distribution facility, a pharmaceutical manufacturing facility, and the like.

Each of the audits 108, 110, 112 may correspond to one or more particular policies. Additionally or alternatively, the audits 108, 110, 112 may correspond to a particular period in time (e.g., a particular period in time at which the audit 108, 110, 112 was completed and/or received) and/or a particular employee (e.g., a self audit by the employee). As depicted, some of the audits 110, 112 stored within the audit database 104 include risk scores 114, 116. The risk scores 114, 116 may have been previously computed (e.g., by the computing system 102 or a similarly-configured computing system). For example, the audits 110, 112 may have been previously completed (e.g., may correspond to an earlier period in time than the audit 108) and the risk scores 114, 116 may have been computed for the audits 110, 112 when the audits 110, 112 were completed and received. As depicted, the risk scores 114, 116 are stored within the audit database 104 in association with audits 110, 112. However, in additional or alternative implementations, the risk scores 114, 116 may be stored separately (e.g., in a separate database communicatively coupled to the computing system 102). In certain implementations, one or more of the audits 108, 110, 112 may correspond to more than one policy (e.g., more than one policy applicable to the healthcare site 106). For example, the audit 108 may have a first portion corresponding to a first policy (e.g., a pharmaceutical storage policy), a second portion corresponding to a second policy (e.g., an employee safety policy), and a third portion corresponding to a third policy (e.g., a sanitization policy).

In certain implementations, the audits 108, 110, 112 may be received directly from employees as the employees complete the audits 108, 110, 112. For example, the employees may enter responses to the audits 108, 110, 112 via one or more computer-based forms and the responses to the audits 108, 110, 112 may be stored within the audit database 104 as the employees complete the audits 108, 110, 112 and/or as the employees enter responses 118. In still further implementations, the audits 108, 110, 112 may be retrieved from other databases storing the audits 108, 110, 112. For example, the audits 108, 110, 112 may be initially stored in databases associated with the stakeholders or other departments who create, monitor, and administer the audits (e.g., according to particular policies associated with the stakeholders or departments). In such instances, different audits 108, 110, 112 associated with different policies and/or different types of healthcare sites 106 may be stored in different databases. As a first example, audit responses for a first type of audit may be received by a Forms On Fire 0 form management system and exported to and stored in a structured query language (SQL) database. As a second example, audit responses for a second type of audit may be received via a web form and stored in a spreadsheet (e.g. a Microsoft Excel® spreadsheet). As a third example, audit responses for a third type of audit may be received via a Google Docs® form and responses may be stored in a Google Sheet®. The audit database 104 may be communicatively coupled to these storage systems (e.g., the SQL database, a storage location for the spreadsheet, the Google Sheet® storing responses) and may extract copies of the audits 108, 110, 112 and/or responses to the audits 108, 110, 112. For example, the audit database 104 may be implemented as a SharePoint® database storing copies of the audits 108, 110, 112 retrieved from other databases. In still further implementations, the audit database 104 may be implemented as other types of databases (e.g., SQL databases, shared directories, relational databases, cloud storage services, and the like). The consolidated storage of audits 108, 110, 112 in this way may form a centralized source of audits in their responses separate from the disparate systems employed by stakeholders and/or departments within a healthcare provider that administer the audits. Such systems may accordingly allow for improved and simpler access to the data (e.g., by the computing system 102, by employees or managers responsible for multiple healthcare sites and/or multiple policies applicable to the healthcare provider).

As depicted, the audit database 104 stores three audits 108, 110, 112 associated with one healthcare site 106. In practice, it should be understood that the audit database 104 may store many more than three audits and may store audits associated with more than one healthcare site 106. For example, the audit database 104 may store tens or hundreds of audits associated with a particular healthcare site 106 and/or may store audits associated with tens, hundreds, or more healthcare sites. Furthermore, the audit database 104 may store multiple types of audits, as explained further below in connection with FIG. 2. Furthermore, the audit database 104 may store audits that are not associated with healthcare sites. For example, the audit database 104 may store audits associated with retail locations, office buildings, transportation systems, or any other business, group, or establishment that performs audits to measure compliance with one or more policies (e.g., safety policies, financial policies, accounting policies). Accordingly, it should be understood that any of the techniques discussed within the present disclosure may be used to measure risks (e.g., to calculate risk scores) associated with healthcare sites and/or for retail locations, office buildings, transportation systems, or any other business, group, or establishment that performs audits.

The computing system 102 may be configured to receive and analyze audits 108 from the audit database 104. For example, the computing system 102 may be configured to receive an audit 108 from the audit database and compute a risk score 120 based on the audit 108. The audit 108 received from the audit database 104 may include responses 118. For example, the response 118 may include answers to questions included within the audit 108. In particular, the responses 118 may be entered by an individual completing the audit 108 for the healthcare site 106. For example, the responses 118 may be entered by an employee or other auditor completing the audit 108. Additionally or alternatively, the responses 118 may include one or more automatically-generated responses (e.g., responses generated by automated or computerized auditing processes of inventory systems, accounting systems, financial systems, and the like).

To compute the risk score 120, the computing system 102 may determine one or more quantities 124, 126, 128, 130 associated with the responses 118. For example, the computing system 102 may determine one or more quantities 124, 126, 128, 130 associated with particular statuses 132, 134, 136 and total responses 138 for the audit 108. As a specific example, the computing system 102 may determine a first quantity 124 of the responses 118 that indicate a deficient status 132 for the healthcare site 106. The deficient status 132 may include any response or status indicating that a condition corresponding to the question or response of the audit 108 is not sufficient to comply the requirements of at least one related policy. As one example, the deficient status 132 may include responses with statuses of "deficient," "unsatisfactory," "needs improvement," and the like. As another example (e.g., where one or more of the responses 118 include a numeric range of 0-10), the deficient status 132 may include a range of values (e.g., 1-5). The computing system 102 may additionally determine a second quantity 126 of the responses 118 that indicates an improvement required status 134. The improvement required status 134 may include any response or status indicating that a condition corresponding to the question or response of the audit 108 required improvement by the healthcare site 106 before achieving compliance. As one example, the improvement required status 134 may include responses with statuses of "improvement needed," "improvement required," "condition corrected," and the like. As another example (e.g., where one or more of the responses 118 include a numeric range of 0-10), the improvement required status 134 may include a range of values (e.g., 6-7). The computing system 102 may further determine a third quantity 128 of the responses 118 that indicate an inapplicable status 136. The inapplicable status 136 may include any response or status indicating that a requirement (e.g., a requirement of a policy) corresponding to the question or response of the audit 108 does not apply to the healthcare site 106. As one example, the inapplicable status 136 may include responses with statuses of "N/A," "not applicable," "not required," "inapplicable," and the like. Furthermore, the inapplicable status 136 may include responses 118 that do not include a response. As another example (e.g., where one or more of the responses 118 include a numeric range of 0-10), the inapplicable status 136 may include a numeric value (e.g., 0). Although not depicted, one or more of the responses 118 may include a satisfactory status. For example, the satisfactory status may include any response or status indicating that a condition corresponding to the question or response of the audit 108 is sufficient to comply with the requirements of at least one related policy. As a specific example, the satisfactory status may include responses 118 indicating "satisfactory," "sufficient," "requirements met," and the like. As another example (e.g., where one or more of the responses 118 include a numeric range of 0-10), a sufficient status may include a range of values (e.g., 8-10).

To determine the quantities 124, 126, 128, the computing system 102 may count the number of responses 118 associated with each status 132, 134, 136. The computing system 102 may also determine a may count the total number of responses 118 as the quantity 130. Additionally or alternatively, and as explained further below, a separate risk score 120 may be calculated for different categories of the audit 108. For example, the audit 108 may include a first category associated with pharmaceutical storage requirements, a second category associated with employee safety requirements, and a third category associated with customer safety requirements. In such instances, the quantities 124, 126, 128 may be determined based on the number of responses in the categories of the audit 108 with the statuses 132, 134, 136 and the quantity 130 of total responses 138 may be based on the total number of responses in the categories of the audit 108. In still further implementations, the audit 108 may include one or more of the quantities 124, 126, 128, 130 for example, the audit 108 may include particular summary statistics indicating at least one of the quantity 124 of responses 118 with a deficient status 132, the quantity 126 of the responses 118 indicating an improvement required status 134, the quantity 128 of the responses 118 indicating an inapplicable status 136, and a quantity 130 of the responses 118 indicating the total responses 138. In such instances, the computing system 102 may extract the quantities 124, 126, 128, 130 from the audit 108, rather than calculating the quantities 124, 126, 128, 130.

The computing system 102 may calculate the risk score 120 based on the quantities 124, 126, 128, 130. In particular, the computing system 102 may calculate a deficiency score 140 and a total score 142 and may calculate the risk score 120 based on the deficiency score 140 and the total score 142. The deficiency score 140 may be calculated as a measure of the healthcare site 106's overall number of responses indicating a failure to comply with a policy (e.g., a policy associated with the audit 108 and/or a policy associated with a category of the audit 108 for which the risk score 120 is being calculated). As a specific example, the deficiency score 140 may be calculated based on the quantity 124 of responses 118 indicating a deficient status 132 and the quantity 126 of responses 118 indicating an improvement required status 134. In certain implementations, the deficiency score 140 may be calculated by adding the quantities 124, 126. In certain implementations, when calculating the deficiency score 140, the quantity 126 of responses 118 indicating an improvement required status 134 may be weighted lower (e.g., to have a lower overall impact on the deficiency score 140) than the quantity 124 of responses 118 indicating a deficient status 132, because the healthcare site 106 has corrected the underlying deficiency.

The total score 142 may be calculated as a measure of the total number of responses 118 applicable to the healthcare site 106. For example, the total score 142 may be calculated based on the quantity 130 of total responses 138 and the quantity 128 of the responses 118 with an inapplicable status 136. In particular, the total score 142 may be calculated by subtracting the quantity 128 from the quantity 130 to determine a total number of responses 118 applicable to the healthcare site 106. The risk score 120 may then be calculated based on the deficiency score 140 and the total score 142. In particular, the risk score 120 may be calculated by dividing the deficiency score 140 by the total score 142. As explained further below, the risk score 120 may further be calculated based on an adjustment value, which may be applied to one or both of the deficiency score 140 and the total score 142 prior to dividing the deficiency score 140 and the total score 142 to generate the risk score 120.

In certain implementations, one or more of the responses 118 may be associated with larger risks (e.g., a higher likelihood of future loss events, a failure to comply with a more important policy requirement, a greater risk of danger to employees, customers, and the like). Accordingly, one or more of the responses 118 may include weighting values (i.e., "risk values"). The risk values assigned to responses 118 associated with larger risks may be higher than risk values assigned to responses 118 associated with smaller risks. As a specific example, a first response may indicate whether the healthcare site 106 complies with a requirement for storing controlled substances and a second response may indicate whether the healthcare site 106 includes proper signage at customer checkout regarding insurance acceptance and processes. In such instances, the first response may include a higher risk value in the second response may include a lower risk value. In implementations where risk values are assigned to the responses 118, the quantities 124, 126, 128, 130 may be computed by adding together the risk values of the associated responses 118. For example, the quantity 124 may be computed by adding together the risk values of responses 118 associated with a deficient status and the quantity 126 may be calculated by adding together the risk values of responses 118 associated with an improvement required status. As another example, the quantity 128 may be computed by adding together the risk values of responses 118 associated with an inapplicable status 136 and the quantity 130 may be computed by summing together the risk values associated with all of the responses 118.

The computing system 102 also includes a user interface 122. The user interface 122 may be used to display risk scores 120 calculated by the computing system 102. For example, the user interface 122 may be used to display the risk score 120 calculated by the computing system 102 and/or other risk scores (e.g., risk scores 114, 116 stored in the audit database 104 or another database). As a particular example, the user interface 122 may generate alerts 144 based on risk scores 120 calculated by the computing system 102. For instance, if a risk score 120 is too high (e.g., exceeds a predetermined threshold), the user interface 122 may generate and display an alert 144 identifying the healthcare site 106 and the risk score 120. The user interface 122 may also generate and display score summaries 146 based on multiple risk scores 114, 116, 120. For instance, the user interface 122 may determine an aggregate risk score 148 one or more healthcare sites associated with a user (e.g., an employee, manager, auditor of multiple healthcare sites including the healthcare site 106). As a specific example, the computing system 102 may combine the most recent risk score 120 associated with the healthcare site 106 with the most recent risk scores for other healthcare sites (e.g., other healthcare sites associated with or managed by the user) to generate an aggregate risk score 148 of the healthcare sites associated with the user. Aggregate risk scores 148 may enable the efficient combination and analysis of responses from multiple audits, including multiple audits regarding multiple healthcare sites and/or multiple policies applicable to the healthcare sites. Additionally or alternatively, the user interface 122 may generate and display a risk trend measurement 150 for a particular healthcare site 106. The risk trend measurement 150 may be calculated as a change in risk and/or a change in policy compliance for a particular healthcare site 106 over time. As a specific example, the audits 110, 112 may have been performed at earlier times than the audit 108. For example, the audit 110 may have been performed 6 months before the audit 108 and the audit 112 may have been performed 12 months before the audit 108. The risk trend measurement 150 for the healthcare site 106 may accordingly be calculated based on the risk score 120 associated with the audit 108 and the risk scores 114, 116 associated with the audits 110, 112. As a specific example, the risk trend measurement 150 may be calculated as an increase or decrease in the risk scores 114, 116, 120 over time (e.g., over the last six months, the last year, the last two years). As another example, the risk trend measurement 150 may be displayed as a trendline of the risk scores 114, 116, 120 over time (e.g., over the last six months, the last year, the last two years). Specific exemplary user interfaces similar to the user interface 122 are discussed in greater detail below in connection with FIGS. 6A-C. Additionally, although the user interface 122 is depicted as part of the computing system 102, it should be understood that, in practice, the user interface 122 may be displayed in a different computing system (e.g., a computing system associated with the user). For example, the different computing system may receive the risk score 120 and any other risk scores 114, 116 needed to generate the alerts 144 and/or score summaries 146 and may generate the user interface 122 for display on the different competing system.

One or more of the computing system 102 and the audit database 104 may be implemented by a computer system. For example, although not depicted, one or both of the computing system 102 and the audit database 104 may include a processor and a memory configured to implement at least one operational feature. In particular, the memory may store instructions which, when executed by the processor, cause the processor to implement the at least one operational feature of the computing system 102 and/or the audit database 104. Additionally, the computing system 102 and the audit database 104 may be configured to communicate via a network. For example, the computing system 102 and the audit database 104 may communicate with the network using one or more wired network interfaces (e.g., Ethernet interfaces) and/or wireless network interfaces (e.g., Wi-Fi®, Bluetooth®, cellular data interfaces). In certain instances, the network may be implemented as a local network (e.g., a local area network) and/or a global network (e.g., the Internet).

FIG. 2 illustrates an audit database 200 according to an exemplary embodiment of the present disclosure. The audit database 200 may be an exemplary implementation of an audit database used by the system 100. For example, the audit database 200 may be an exemplary implementation of the audit database 104. As explained above, audit databases 200 may store multiple audits and may store different types of audits. For example, audits stored by audit databases 200 may correspond to different policies, different parts of policies, and/or different healthcare sites. Furthermore, the audit database 200 may store audits prepared by different individuals and/or different entities. For example, the audit database 200 stores multiple audits 204, 206, 208, 210, 212, 214, 216, 218, 220 that have different types. In particular, the audits 204, 206, 208, 210 are self audits, the audits 212, 214, 216 are on-site audits, the audit 218 is a regional audit, and the audit 220 is an off-site audit.

Self audits 204, 206, 208, 210 may include audits completed by managers or other individuals responsible for the operation of individual healthcare sites. For example, self audits 204, 206, 208, 210 may include responses regarding policy requirements applicable to individual healthcare sites (e.g., a particular healthcare site managed or supervised by the individual preparing the self audit 204, 206, 208, 210). In certain implementations, employees may complete self audits 204, 206, 208, 210 on a regular basis. For example, self audits 204, 206, 208, 210 may be completed weekly, monthly, quarterly, and/or semiannually. In certain instances, self audits 204, 206, 208, 210 may also be referred to or identified as internal audits or manager audits.

On-site audits 212, 214, 216 may include audits completed by individuals independent from particular healthcare sites, managers or other individuals responsible for the operation of individual healthcare sites. For example, on-site audits 212, 214, 216 may include responses regarding policy requirements applicable to the individual healthcare sites and may be filled in by third-party auditors hired by the healthcare site and/or a healthcare provider associated with the healthcare site. In certain implementations, on-site audits 212, 214, 216 may be completed on a regular basis, but may be completed less frequently than self audits 204, 206, 208, 210. For example, on-site audits 212, 214, 216 may be completed quarterly, semiannually, and/or annually.

Regional audits 218 may include audits completed by managers, supervisors (e.g., regional supervisors), or other individuals responsible for the operation of multiple healthcare sites (e.g., multiple healthcare sites located within a particular region). For example, regional audits 218 may include policy requirements applicable to a particular healthcare site (e.g., a particular healthcare site managed by the individual preparing the regional audit 218). In particular, individuals such as regional managers may regularly visit the healthcare sites they manage to perform regional audits 218. For example, regional audits 218 may be completed quarterly, semiannually, and/or annually. In certain instances, regional audits 218 may also be referred to or identified as supervisor audits.

Off-site audits 220 may include audits completed by individuals independent from particular healthcare sites. For example, off-site audits 220 may be completed by independent auditors not associated with a healthcare provider operating a healthcare site. For example, off-site audits 220 may include policy requirements applicable to a particular healthcare sites (e.g., a particular healthcare site visited by an independent auditor). In particular, individual auditors may regularly visit healthcare sites to perform off-site audits 220. For example, off-site audits 220 may be completed semiannually and/or annually.

In certain implementations, audits 204, 206, 208, 210, 212, 214, 216, 218, 220 of different types may include similar or identical questions. For example, on-site audits 212, 214, 216 may include one or more questions that are identical to questions in regional audits 218 and/or off-site audits 220. Additionally, different audits 204, 206, 208, 210, 212, 214, 216, 218, 220 of the same type may have different questions. For example, self audits 204, 206, 208, 210 may have a rotating set of questions. Accordingly, successive self audits 204, 206, 208, 210 completed by an individual may have different questions from one another. In certain implementations, self audits may be generated such that the employee completing the self audits sees each question at least once in a predetermined amount of time (e.g., once every month, once every six months, once every year) and/or at least once in a predetermined number of audits (e.g., once every three audits, once every five audits, once every 10 audits).

Several of the audits 208, 210, 216 within the audit database 200 are depicted with dashed lines. Such audits 208, 210, 216 may still be in progress. For example, responses may not have been received for all of the questions within the audits 208, 210, 216. In particular, employees or auditors may still be completing the audits 208, 210, 216. As another example, responses may have been received for all of the questions within the audits 208, 210, 216. However, certain responses associated with particular requirements may have indicated a deficient status 132. In such instances, the associated employee and/or healthcare site may be required to correct one or more conditions or practices in order to comply with the requirements associated with responses having a deficient status. While the corrections are implemented, the audits 208, 210, 216 may be considered incomplete. Once the corrections have been implemented and verified, the responses with a deficient status 132 may be updated to have an improvement required status 134 and the audits 208, 210, 216 may be considered complete at that time.

Figure 3:
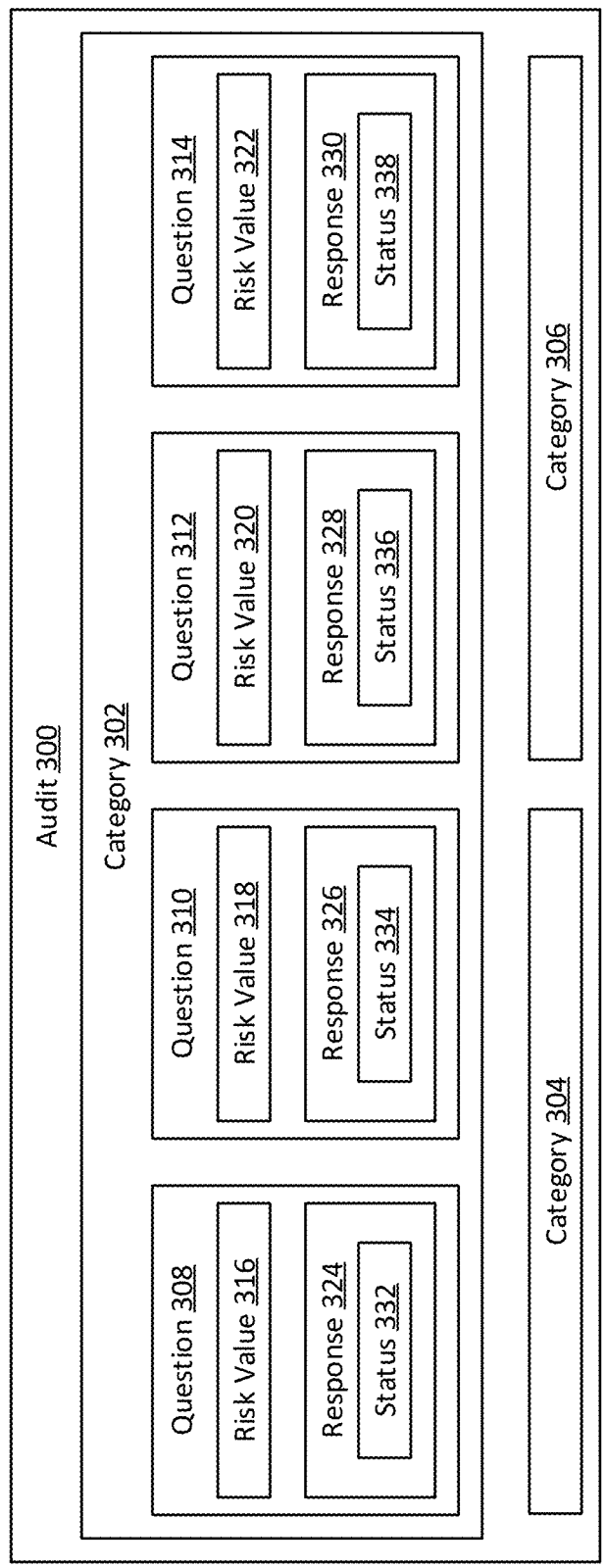
FIG. 3 illustrates an audit according to an exemplary embodiment of the present disclosure.

FIG. 3 illustrates an audit 300 according to an exemplary embodiment of the present disclosure. The audit 300 may be an exemplary implementation of an audit analyzed by the computing system 102. For example, the audit 300 may be an exemplary implementation of the audit 108. Additionally or alternatively, the audit 300 may be an exemplary implementation of an audit stored by an audit database 104, 200. For example, the audit 300 may be an exemplary implementation of the audits 110, 112, 204, 206, 208, 210, 212, 214, 216, 218, 220.

The audit 300 contains multiple categories 302, 304, 306. The categories 302, 304, 306 may include different types of questions. For example, the categories 302, 304, 306 may be associated with, e.g., different policies, different types of policies, different types of requirements under a particular policy, different types of policy requirements for multiple policies. In one specific example, the category 302 may be associated with requirements for pharmaceutical storage, the category 304 may be associated with requirements for employee safety, and the category 306 may be associated with requirements for customer safety.

The category 302 includes multiple questions 308, 310, 312, 314. Although not depicted, the categories 304, 306 may similarly include multiple questions 308, 310, 312, 314. The questions 308, 310, 312, 314 may be applicable to the policy or type of policy requirement associated with the category 302. In certain implementations, certain questions 308, 310, 312, 314 may correspond to a particular policy requirement, certain questions may correspond to multiple policy requirements, and/or certain policy requirements may have multiple corresponding questions 308, 310, 312, 314 within the category 302.

The questions 308, 310, 312, 314 include risk values 316, 318, 320, 322. As explained above, the risk values 316, 318, 320, 322 may be assigned to indicate a relative importance and/or relative severity of future risk events. For example, risk values 316, 318, 320, 322 may be higher for questions associated with a higher likelihood of risk events and/or a greater amount of policy noncompliance. In certain implementations, the risk values 316, 318, 320, 322 may be assigned by domain experts (e.g., by individuals and/or committees preparing the audit 300). Additionally or alternatively, the risk values 316, 318, 320, 322 may be at least partially generated and/or adjusted automatically. For example, the risk values 316, 318, 320, 322 may be created at least in part by a machine learning model. For example, the machine learning model may be trained on data regarding past audits of noncompliant healthcare sites and/or on past audits of healthcare sites that experienced risk events (e.g., risk events associated with the category 302). Based on the past audits, the machine learning model may identify particular questions 308, 310, 312, 314 that are more likely or less likely to be associated with a risk event and/or noncompliance with a policy or policy requirement associated with the category 302. In such instances, questions 308, 310, 312, 314 that are more likely to be associated with a risk event or noncompliance may be given a higher risk value 316, 318, 320, 322 and questions 308, 310, 312, 314 that are less likely to be associated with a risk event or noncompliance may be given a lower risk value 316, 318, 320, 322. In still further implementations, the risk values 316, 318, 320, 322 may be determined at least in part based on a number of corresponding policy requirements for the questions 308, 310, 312, 314. For example, questions 308, 310, 312, 314 associated with more policy requirements may be assigned a larger risk value 316, 318, 320, 322.

The questions 308, 310, 312, 314 include responses 324, 326, 328, 330. The types of responses 324, 326, 328, 330 received may differ by the type of question 308, 310, 312, 314. In certain implementations, one or more of the questions 308, 310, 312, 314 may include predesignated options that can be used for providing responses 324, 326, 328, 330. For example, the predesignated options may include one or more of "satisfactory," "deficient," "improvement needed," and/or "not applicable." One or more of the questions 308, 310, 312, 314 may include a numeric range that may be used for responses 324, 326, 328, 330. For example, certain questions 308, 310, 312, 314 may use a numeric range of 0-10, with 0 indicating that a particular question 308, 310, 312, 314 is not applicable to a healthcare site. In still further implementations, one or more of the questions 308, 310, 312, 314 may include free text entry for responses 324, 326, 328, 330, which may allow users to type or otherwise enter text associated with the questions 308, 310, 312, 314.

The responses 324, 326, 328, 330 include statuses 332, 334, 336, 338. As explained above, the statuses 332, 334, 336, 338 may indicate a satisfactory status, a deficient status 132, an improvement required status 134, and/or an inapplicable status 136. In certain instances, the statuses 332, 334, 336, 338 indicated by each of the responses 324, 326, 328, 330 may be determined based on the contents of the responses 324, 326, 328, 330. For example, where the responses 324, 326, 328, 330 include predesignated options, particular predesignated options may correspond to particular statuses 332, 334, 336, 338. As one specific example, where a response 324 indicates "satisfactory," the corresponding status 332 may be determined to be the satisfactory status. As another example, where a response 326 indicates "not applicable," the corresponding status 334 may be determined to be the inapplicable status 136. In further implementations, statuses 332, 334, 336, 338 for responses 324, 326, 328, 330 containing numeric values may be determined based on the numeric value. For example, where responses 324, 326, 328, 330 are entered as a number within the range of 0-10, a satisfactory status may be determined for responses 324, 326, 328, 330 with a numeric value of 8-10, an improvement required status 134 may be determined for responses 324, 326, 328, 330 with a numeric value of 6-7, a deficient status 132 may be determined for responses 324, 326, 328, 330 with a numeric value of 1-5, and an inapplicable status 136 may be determined for responses 324, 326, 328, 330 with a numeric value of 0. In still further implementations, where responses 324, 326, 328, 330 are entered as free text, the contents of the text entered by an individual preparing the audit may be analyzed to determine the status. For example, keyword searches or other analyses may be performed on the contents of the text to determine a particular status 332, 334, 336, 338. As one specific example, to determine a deficient status 132, a keyword search may be performed for responses 324, 326, 328, 330 containing "noncompliant," "unsatisfactory," "needs improvement," "bad," "insufficient," and the like.

Figure 4:
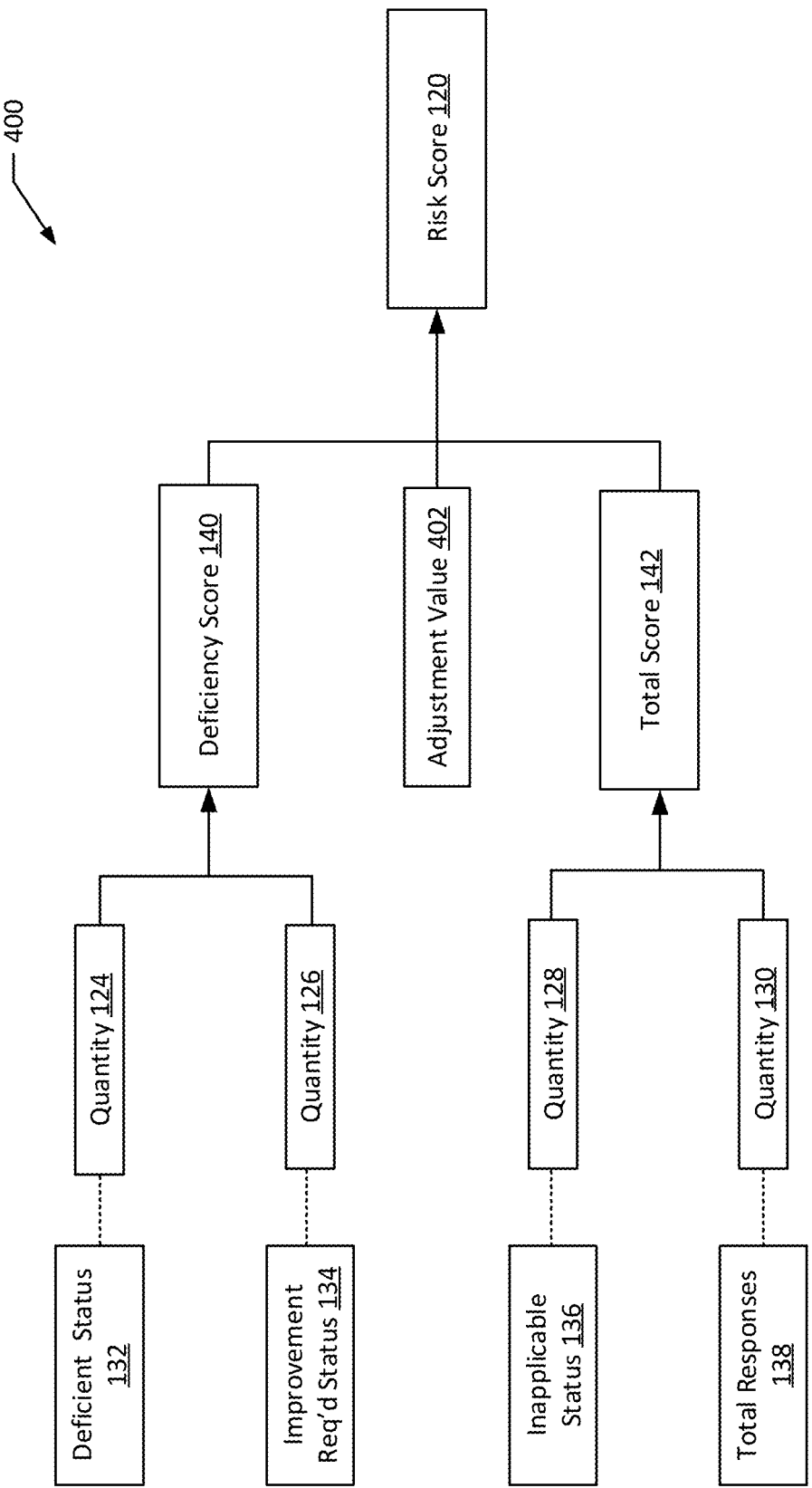
FIG. 4 illustrates a risk score calculation procedure according to an exemplary embodiment of the present disclosure.

FIG. 4 illustrates a risk score calculation procedure 400 according to an exemplary embodiment of the present disclosure. The risk score calculation procedure 400 may be performed to calculate a risk score 120. For example, the risk score calculation procedure 400 may be performed by the computing system 102 to calculate the risk score 120. The risk score calculation procedure 400 begins with determining quantities 124, 126, 128, 130 of responses 118 of an audit 108 and/or a category of an audit 108 for which the risk score 120 is to be calculated. For example, and as explained above, the computing system 102 may determine a quantity 124 of the responses 118 with a deficient status 132, a quantity 126 of the responses 118 with an improvement required status 134, a quantity 128 of the responses 118 with an inapplicable status 136, and a quantity 130 of total responses 138 in the audit 108 or category for which the risk score 120 is being calculated.

The deficiency score 140 may be calculated based on the quantity 124 and the quantity 126. For example, the deficiency score 140 may be computed by adding the quantities 124, 126. In certain implementations, weights may be applied to the quantities 124, 126 before adding the quantities 124, 126 together to generate the deficiency score 140. For example, a first weight may be applied to the quantity 124 and a second weight and be applied to the quantity 126. In such instances, the first weight may be greater than the second weight. For example, the first weight applied to the quantity 124 may be at least two times larger than the second week. In a preferred implementation, the first weight may be 1 and the second weight may be 0.5, such that:

$$1 * \text{Quantity } 124 + 0.5 * \text{Quantity } 126 = \text{Deficiency Score } 140.$$

The total score 142 may be calculated based on the quantity 128 in the quantity 130. For example, the total score 142 may be calculated by subtracting the quantity 128 from the quantity 130 to determine a total number of the responses 118 that apply to the healthcare site 106 for which the risk score 120 being calculated. Accordingly, the total score 142 may be calculated as:

$$\text{Quantity } 130 - \text{Quantity } 128 = \text{Total Score } 142$$

The risk score 120 may be calculated based on the deficiency score 140 the total score 142. For example, the risk score 120 may be calculated by dividing the deficiency score 140 by the total score 142. In certain implementations, the risk score 120 may further be calculated based on an adjustment value 402. For example, the adjustment value 402 may be subtracted from the deficiency score and the total score 142 prior to dividing the scores 140, 142, such that:

$$\frac{\text{Deficiency Score } 140 - \text{Adjustment Value } 402}{\text{Total Score } 142 - \text{Adjustment Value } 402} = \text{Risk Score } 120$$

In certain implementations, the adjustment value 402 may be determined based on the total score 142. For example, the adjustment value 402 may be computed as:

$$\text{Total Score } 142 * x = \text{Adjustment Value } 402,$$

where x is a configurable value that may be selected to adjust the value of the adjustment value 402 to achieve a desired sensitivity of the risk score calculation. For example, healthcare sites 106 with high risk scores 120 (e.g., risk scores that are above a predetermined threshold) may be visited by auditors, managers, or other employees of a healthcare provider to confirm whether the healthcare sites 106 actually present a large risk. During such visits, it may be determined that at least some of the healthcare sites 106 do not present a large operating risk to the healthcare provider and accordingly should not have high risk scores. In such instances, the adjustment value 402 may be increased (e.g., by increasing x), thereby lowering the risk scores 120. In still further instances, certain healthcare sites 106 with marginally high risk scores 120 (e.g., risk scores that are below, but near, the predetermined threshold used to identify high risk scores) may similarly be visited to determine whether the healthcare sites 106 actually present a low operating risk to the healthcare provider. During such visits, it may be determined that at least some of the healthcare sites 106 do present a large operating risk to the healthcare provider and accordingly should have high risk scores. In such instances, the adjustment value 402 may be decreased (e.g., by decreasing x), thereby increasing the risk scores 120.

Such errors in the risk scores 120 may result from multiple sources. For example, if risk values in the audit 108 are too high or are unbalanced, deficient statuses 132 or improvement required statuses 134 in responses associated with these questions may result in a risk score 120 is higher than warranted. Additionally or alternatively, audits may include a disproportionate number of questions focusing on particular requirements. Accordingly, a deficient condition or a condition requiring improvement associated with the particular requirements may result in a disproportionate number of questions with deficient statuses 132 or improvement required statuses 134, thereby unduly increasing the risk score 120. The adjustment value 402 may be adjusted or updated manually, e.g., based on visits to healthcare sites as described above. Additionally or alternatively, the adjustment value 402 may be updated on an ongoing basis by an automated process (e.g., a computer-implemented process). For example, the adjustment value 402 may be updated by a machine learning model. In particular, the machine learning model may receive indications from follow-up visits to healthcare sites indicating which healthcare sites should have high-risk scores and which healthcare sites should not have high risk scores. The machine learning model may then update the adjustment value 402 to maximize the number of healthcare sites correctly identified with high risk scores and correctly identified with low risk scores.

In still further implementations, different categories 302, 304, 306 of an audit 300 may have different adjustment values. For example, different categories 302, 304, 306 may have separate risk scores calculated. In such instances, different adjustment values may be used for the calculation of risk scores associated with different categories 302, 304, 306. The adjustment values associated with different categories 302, 304, 306 may be updated using techniques similar to those discussed above. For example, adjustment values for different categories 302, 304, 306 may be updated based on visits to healthcare sites with high or marginally high risk scores (e.g., high or marginally high overall risk scores, high or marginally high risk scores in a particular category 302, 304, 306). In such instances, the adjustment values for each category 302, 304, 306 may be updated based on indications received as a result of the visits identifying which healthcare sites should have high risk scores and which healthcare sites should not have high risk scores.

Relatedly, risk scores for different categories 302, 304, 306 of an audit 300 may be combined to identify an overall risk score for a healthcare site 106 associated with the audit 300. For example, the risk score 120 may be calculated for a category 302 of the audit 300. Additional risk scores may similarly be calculated for the categories 304, 306 of the audit 300. Accordingly, to determine the overall risk score for the audit 300, the risk score 120 for the category 302 may be combined with the risk scores of the other categories 304, 306. For example, the risk scores may be added together to generate the overall risk score. As another example, an average of the risk scores may be taken to generate the overall risk score. In certain implementations, the risk scores associated with different categories 302, 304, 306 may receive different weights prior to being combined. For example, the risk score of category 302 may have a weight of 0.5, the risk score of the category 304 may have a weight of 0.3, and the risk score of the category 306 may have a weight of 0.2.

Additionally or alternatively, the risk score 120 of the healthcare site 106 may be combined with other risk scores of different healthcare sites to generate an aggregate risk score 148. For example, a user responsible for managing multiple healthcare sites may request an aggregate risk score 148 for the healthcare sites that the user manages or supervises. In such instances, risk scores associated with the healthcare sites may be identified (e.g., in an audit database 104 or a similar database) and may be combined to generate the aggregate risk score. For example, the risk scores may be added together to generate the aggregate risk score 148. Additionally or alternatively, the aggregate risk score 148 may be generated as an average of the risk scores for the healthcare sites. In certain implementations, risk scores associated with different healthcare sites may be weighted prior to being combined to generate the aggregate risk score 148. For example, the risk scores may be weighted according to the size of the healthcare sites, number of employees working at the healthcare sites, sales volume at the healthcare sites, and the like. As a specific example, stores with larger sales volumes and/or larger number of employees may be weighted higher than stores with lower sales volumes and/or a smaller number of employees.

Risk scores 120 of a healthcare site 106 may also be compared to previous risk scores of the healthcare site 106. For example, previous risk scores 114, 116 may be identified or received (e.g., from an audit database 104 or a similar database) and may be combined with the risk score 120 to generate a risk trend measurement 150 for the healthcare site 106. For example, the risk trend measurement 150 may be calculated as a total change in the risk score 120 relative to the previous risk scores (e.g., in the last six months, in the last year, the last two years). As another example, the risk trend measurement 150 may be calculated as a trendline or a slope of a trendline fitted to the risk score 120 and the previous risk scores (e.g., over the last six months, over the last year, over the last two years). As a further example, the risk trend measurement 150 may be computed or displayed as a moving average of the risk score 120 and the previous risk scores 114, 116.

Figure 5:
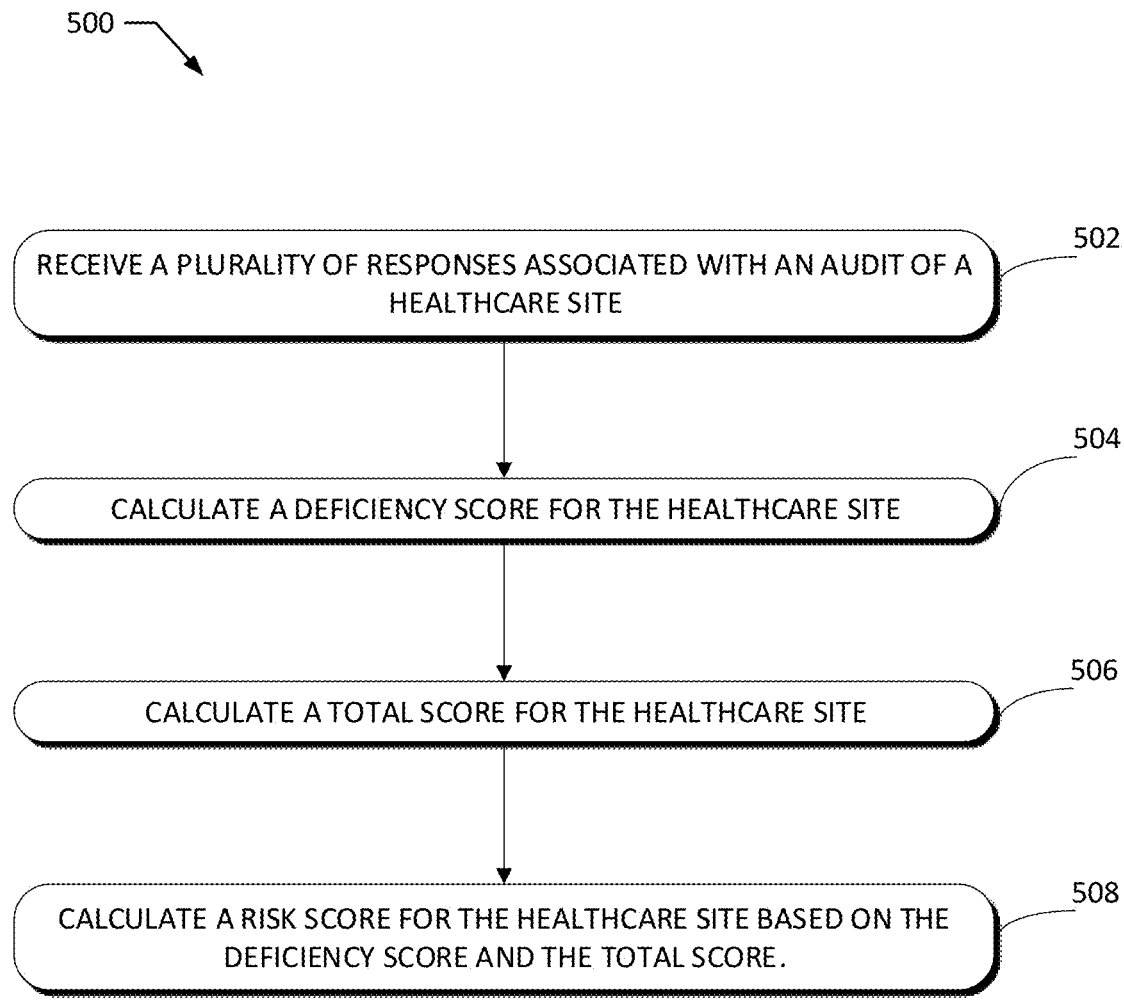
FIG. 5 illustrates a method for calculating risk scores for health sites according to an exemplary embodiment of the present disclosure.

FIG. 5 illustrates a method 500 for calculating risk scores for healthcare sites according to an exemplary embodiment of the present disclosure. In particular, the method 500 may be performed to calculate risk scores 120 for healthcare sites 106 based on audits 108 of the healthcare sites 106. The method 500 may be implemented on a computing system, such as the system 100. For example, the method 500 may be implemented by the computing system 102. The method 500 may also be implemented by a set of instructions stored on a computer-readable medium that, when executed by a processor, cause the computer system to perform the method 500. For example, all or part of the method 500 may be implemented by a processor and a memory of the computing system 102. Although the examples below are described with reference to the flowchart depicted in FIG. 5, many other methods of performing the acts associated with FIG. 5 may be used. For example, the order of some of the blocks may be changed, certain blocks may be combined with other blocks, one or more of the blocks may be repeated, and some of the blocks described may be optional.

The method 500 may begin with receiving a plurality of responses 118 associated with an audit 108 of a healthcare site 106 (block 502). For example, the computing system 102 may receive the audit 108 and/or the responses 118 from an audit database 104 and/or from an employee completing the audit of the healthcare site 106. As explained above, the audit 108 may include multiple categories, and the responses 118 may correspond to a single category within the audit 108 and/or may correspond to multiple categories within the audit 108. The received responses 118 may have one or more formats. For example, certain responses may be selections between particular, predesignated options, certain responses may be a numerical value within a numerical range (e.g., 0-10), and certain responses may include free text entry entered by an employee or individual completing the audit 108. In certain instances, the plurality of responses received may include responses associated with multiple audits (e.g., multiple audits associated with the healthcare site 106, multiple audits associated with multiple healthcare sites).

A deficiency score 140 may be calculated for the healthcare site 106 (block 504). For example, the computing system 102 may calculate the deficiency score 140 based on the responses 118. In particular, the computing system 102 may identify a quantity 124 of the responses 118 indicating a deficient status 132 and a quantity 126 of the responses 118 indicating an improvement required status 134. The computing system 102 may calculate the deficiency score 140 based on the quantity 124 and the quantity 126. For example, as explained further above, the deficiency score 140 may be calculated by adding together the quantities 124, 126, or weighted combinations thereof.

A total score 142 may be calculated for the healthcare site (block 506). For example, the computing system 102 may calculate the total score 142 based on the responses 118. In particular, the computing system 102 may determine a quantity 128 of the responses 118 indicating an inapplicable status 136 and the quantity 130 of the total responses 138. The total score 142 may be calculated to determine a total number of the responses 118 that apply to healthcare site 106. For example, the total score 142 may be calculated by subtracting the quantity 128 from the quantity 130. As explained further above, one or more of the responses 118 may include risk values. In such implementations, the quantities 124, 126, 128, 130 and the corresponding calculations of the deficiency score 140 and the total score 142 may be calculated based on the risk values. For example, the quantities 124, 126, 128 may be calculated by summing the risk values of the responses 118 indicating the associated statuses 132, 134, 136.

A risk score 120 may be calculated for the healthcare site 106 based on the deficiency score 140 and the total score 142 (block 508). For example, the risk score 120 may be calculated by comparing the deficiency score 140 to the total score 142. In particular, the score 120 may be calculated by dividing the deficiency score 140 by the total score 142. In certain implementations, as explained further above, an adjustment value may be subtracted from the deficiency score 140 and/or the total score 142 before dividing. The risk score 120 calculated at block 508 may be combined with other risk scores. For example, where the risk score 120 is calculated for a particular category within an audit 108, the risk score 120 may be combined with risk scores for other categories (e.g., all categories, a subset of categories) within the audit (e.g., in a weighted combination) to determine an overall risk score for the audit 108. For example, where the risk score 120 is calculated for a category of the audit 108 concerning security (i.e., facility security upkeep and maintenance), risk score 120 may be combined with risk scores calculated for other security-related categories of the audit 108 (e.g., controlled substances security practices, invoice security practices) to generate an overall risk score for the security practices of the healthcare site 106. In certain instances, the risk score 120 may be combined with risk scores calculated based on different types of audits. For example, overall risk scores for healthcare sites may be calculated based on two or more of the most recent on-site audits, the most recent regional audit, and the most recent off-site audit. In such instances, where the risk score 120 is calculated based on the most recent on-site audit, the risk score 120 may be combined with a risk score calculated based on the most recent regional audit and/or the most recent off-site audit (e.g., whichever was completed most recently between the two) to generate an overall risk score for the healthcare site. For example, in certain implementations, blocks 504-508 may be repeated to generate a second score based on the most recent regional audit and/or the most recent off-site audit, which may then be combined with (e.g., averaged with) the risk score 120 to calculate the overall risk score 120 for the healthcare site 106.

Performing the method 500 allows computing systems to calculate risk scores for healthcare sites. In particular, the method 500 enables risk scores to be calculated in a way that allows for automated, repeatable calculation of risk scores for multiple audits of multiple healthcare sites. In this way, the method 500 replaces the tedious, manual, and error-prone techniques that are used in existing systems as a result of the disparate preparation and storage of audits and responses. Furthermore, standardized and repeatable techniques for calculating risk scores across healthcare sites and over time enable improved comparisons across different healthcare sites and for the same healthcare site over time. In this way, the method 500 enables improved identification of healthcare sites that present operating risks, enabling earlier risk-prevention interventions, thereby improving the quality and/or safety of healthcare services provided at the healthcare site 106.

Figure 6A:
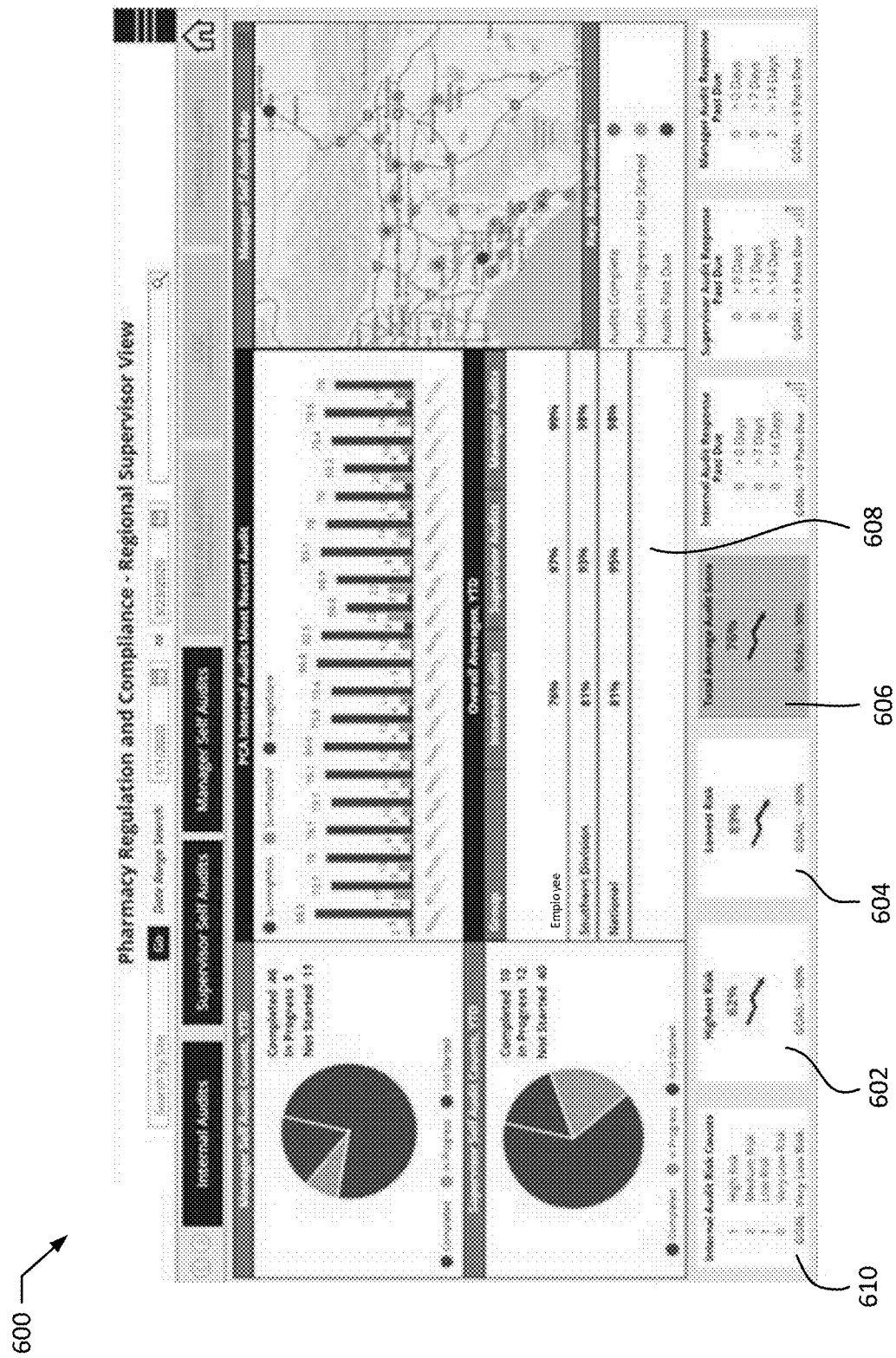
FIGS. 6A-6C illustrate user interfaces according to exemplary embodiments of the present disclosure.
Figure 6B:
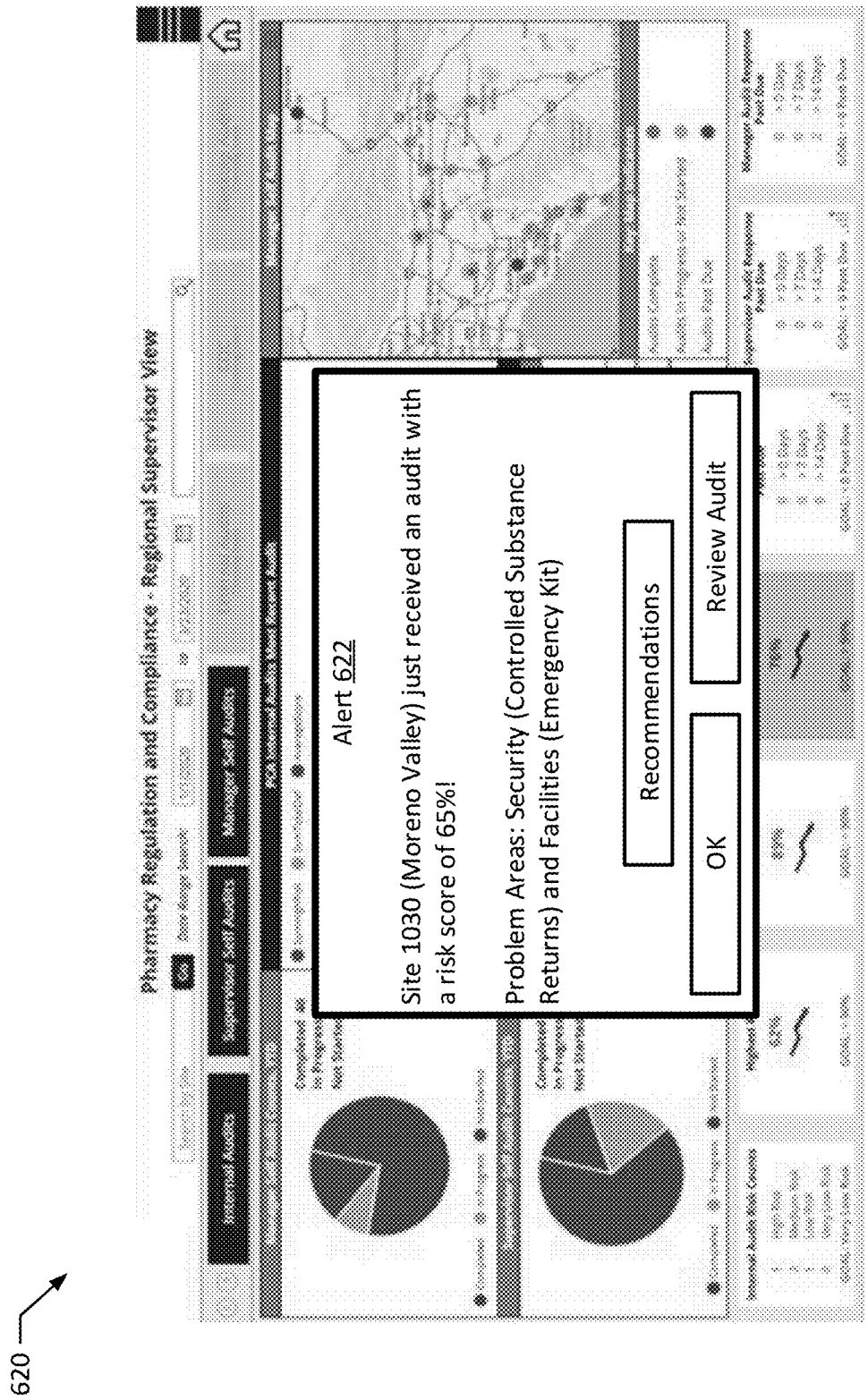
Figure 6C:
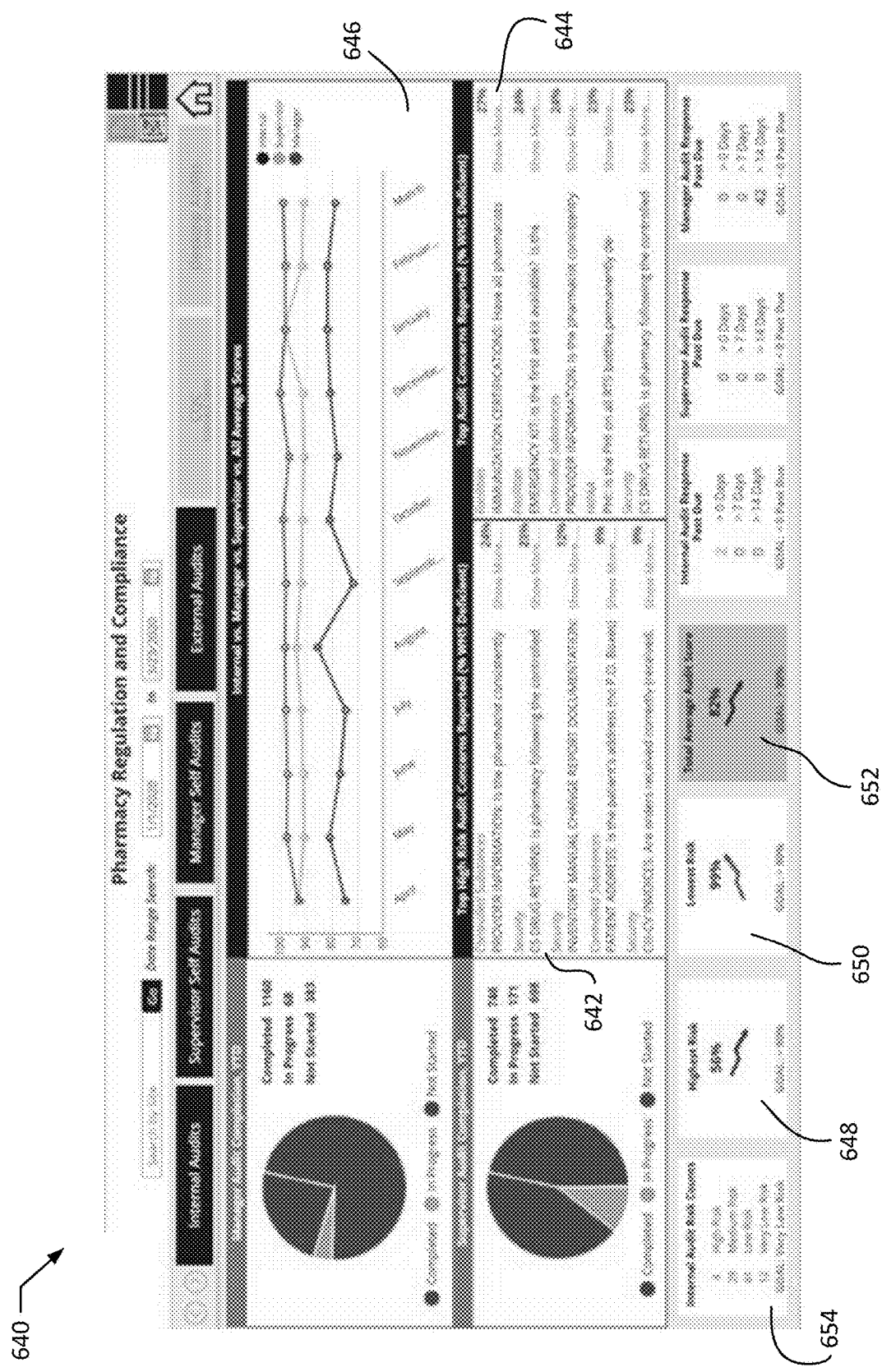

FIGS. 6A-6C illustrate user interfaces 600, 620, 640 according to exemplary embodiments of the present disclosure. The user interfaces 600, 620, 640 may be displayed as interfaces on a computing device. For example, the computing system 102 or another computing system implemented in the user interface 122 may display the user interfaces 600, 620, 640. In certain implementations, the user interfaces 600, 620, 640 may be generated and displayed by software locally stored and hosted on the computing systems 102. Additionally or alternatively, the user interfaces 600, 620, 640 may be accessed via an Internet interface (e.g., using a web browser).

The user interfaces 600, 620, 640 may depict user interfaces for different types of employees within a healthcare provider. For example, the user interfaces, 600, 620, 640 may present information regarding multiple healthcare sites for employees responsible for management and/or operation of the multiple healthcare sites. It should be noted that, in the depicted examples, the displayed risk scores are inverted from those discussed above. Namely, in the depicted examples for the user interfaces 600, 620, 640, higher risk scores are considered better (e.g., indicating more compliance with policy requirements) than lower risk scores. In certain implementations, the depicted risk scores may be calculated by subtracting the risk scores as calculated above from 1. For example, the depicted risk scores may be calculated as:

$$1 - \frac{\text{Deficiency Score } 140 - \text{Adjustment Value } 402}{\text{Total Score } 142 - \text{Adjustment Value } 402} = \text{Risk Score } 120$$

It should be understood that, in different implementations of the user interfaces 600, 620, 640, either formulation of the risk scores may be used.

Turning to FIG. 6A, the user interface 600 depicts an audit dashboard that may be used by an employee responsible for multiple stores (e.g., a regional manager or supervisor). The user interface 600 includes information regarding audit completion percentages for the stores and/or employees associated with (e.g., managed by) the employee. For example, the user interface 600 includes information regarding a number of audit responses that are past due, a number of audits that are completed, a number of audits that are in progress, and a number of audits that have not been started. As depicted, on the left side of the user interface 600, different information is broken out by different types of audits (e.g., manager-completed audits and supervisor-completed audits). An additional or alternative implementation, statistics regarding audit completion may be subdivided by store, by individual employee, by division (e.g., regional division). Statistics may also be broken out on a national level, on a state level, or by department (e.g., within the same department spread across multiple healthcare sites).

The user interface 600 also provides summary statistics regarding risk scores calculated for different healthcare sites. For example, the user interface 600 may generate summary statistics regarding the most recently calculated risk scores (e.g., risk scores calculated based on the most recently-completed audits) for the healthcare sites associated with the employee. In particular, the user interface 600 includes an averages section 608 depicting average risk scores associated with different types of audits (e.g., internal audits, supervisor audits, manager audits). In particular, the averages section 608 includes the average scores associated with the employee for whom the user interface 600 is generated, along with average scores in the southern division and on a national level. The employee may supervise stores located in the southern division, and grouping the audit scores in this way may enable quicker comparison of risk scores calculated for stores associated with the employee to similar stores (e.g., stores in the same division) and/or a national level of risk score.

Further risk score summary statistics associated with the employee for which the user interface 600 was generated are depicted at the bottom of the user interface 600. In particular, the user interface 600 includes a highest risk portion 602, a lowest risk portion 604, and an average score portion 606. The highest risk portion 602 identifies the risk score associated with the highest risk healthcare site. In particular, the highest risk portion 602 indicates that the highest risk healthcare site has a risk score of 62%. The highest risk portion 602 also includes a risk trend measurement (e.g., a trendline indication) below the risk score depicting a downward sloping arrow, indicating that the risk score associated with the highest risk healthcare site has been decreasing recently (e.g., over the previous six months, previous 12 months, previous 24 months). In certain implementations, the highest risk portion 602 may be clickable by a user. For example, after clicking the highest risk portion 602 a new user interface may be displayed that includes information regarding the highest risk healthcare site (e.g., recent audits, high-risk audit responses, contact information, responsible employee information). The lowest risk portion 604 identifies the risk score associated with the lowest risk healthcare site. In particular, the lowest risk portion 604 indicates that the hope lowest risk healthcare site has a risk score of 89%. Similar to the highest risk portion 602, the lowest risk portion 604 includes a risk trend measurement as a trendline indication sloping downward, indicating that the risk score associated with the lowest risk healthcare site has been recently decreasing. Furthermore, similar to the highest risk portion 604, the lowest risk portion 604 may be clickable to view information regarding the lowest risk healthcare site. The average score portion 606 may display an average risk score for healthcare sites associated with the employee. For example, the average score portion 606 indicates that the average risk score associated with healthcare sites manager supervised by the user is 76%. Furthermore, the average score portion 606 includes a risk trend measurement indicating that the average risk score for the healthcare sites has been decreasing recently.

The user interface 600 also includes a risk count portion 610, which may be generated to include counts of healthcare sites with particular quantities 124 of responses with a deficient status ("deficient responses"). For example, the risk count portion 610 includes counts of healthcare sites in high risk, medium risk, low risk, and very low risk categories. In particular, the high risk category may include healthcare sites with 30 or more deficient responses, the medium risk category may include healthcare sites with 20-29 deficient responses, the low risk category may include healthcare sites with 6-19 deficient responses, and the very low risk category may include healthcare sites with 5 or fewer deficient responses.

In additional or alternative implementations, the risk count portion may include counts of healthcare sites with risk scores or deficiency scores that fall in the particular categories. For example, the risk count portion 610 includes counts of healthcare sites in high risk, medium risk, low risk, and very low risk categories. In particular, the high risk category may include healthcare sites with audit scores below 65%, the medium risk category may include healthcare sites with audit scores below 75%, the low risk category may include healthcare sites with audit scores below 90%, and the very low risk category may include healthcare sites with audit scores greater than or equal to 90%. It should be understood that alternative implementations of the categories may be possible (e.g., using different cutoff points or thresholds). As depicted, the user has one associated healthcare site in the high risk category, two associated healthcare sites in the medium risk category, one associated healthcare site in the low risk category, and zero associated healthcare sites in the very low risk category.

In certain implementations, alerts may be presented by the user interfaces. For example, alerts may be presented when particular healthcare sites (e.g., particular healthcare sites associated with a user of the user interface) receive new risk scores indicating a particular risk level (e.g., risk scores above or below a predetermined threshold), receives a risk response associated with a high-risk policy requirement (e.g., a deficient status to a question with a high risk value), and/or completes improvements required to comply with a policy requirement indicated by a previous audit. In certain implementations, alerts may be overlaid over user interfaces, such as the user interface 600. In particular, FIG. 6B depicts a user interface 620 in which the user interface 600 is overlaid with an alert 622. The alert 622 identifies a particular healthcare site and includes a site ID 1030 (e.g., a numeric identifier of the healthcare sites) and a location of the healthcare site (i.e., Moreno Valley). The alert 622 also indicates information regarding the cause of the alert 622. Namely, the alert 622 indicates that site 1030 received an audit with an unsatisfactory risk score of 65%. Where an alert is presented in response to a particular audit, the alert may also present further information summarizing the contents of the audit. For example, the alert 622 includes indications of problem areas (e.g., categories of the audit that contributed most to the unsatisfactory risk score). In particular, the alert 622 indicates that responses concerning security, namely controlled substance returns, and facilities, namely emergency kit responses, contributed most to the risk score of the healthcare site. Such implementations may expedite the preparation and implementation of corrections necessary to improve the risk scores of healthcare sites, thereby bringing the healthcare sites into greater compliance with applicable policies and requirements. Furthermore, alerts may further present the opportunity to review the audit that resulted in the unsatisfactory risk score and/or may present recommendations for addressing the problem areas. For example, the alert 622 includes a clickable button to review the audit. Clicking the review audit button may display a different user interface that includes information regarding the audit (e.g., questions, responses, further summary statistics regarding the audit) that resulted in the unsatisfactory risk score that triggered the alert 622. The alert 622 also includes a clickable button to review recommendations. Clicking the recommendations button may display one or more recommendations (e.g., corrections, training, changes in policy) for addressing the problem areas identified in the audit. In certain implementations, the recommendations may be automatically generated and/or identified. For example, the system 100 may further include a database storing corrective actions taken in response to particular unsatisfactory audit responses (e.g., deficient status responses in particular categories or in response to particular questions). Recommendations may be identified by locating similar responses and/or similar questions and extracting the corrective actions associated with the similar responses and/or similar questions. The extracted corrective actions may be presented as recommendations. Additionally or alternatively, recommendations may be manually created and entered in association with individual questions and/or categories of audits.

Turning to FIG. 6C, the user interface 640 depicts an audit dashboard that may be used by an employee responsible for many healthcare sites, such as all of the healthcare sites associated with a particular healthcare provider. For example, the user interface 640 may be presented to a user that is an executive of the healthcare provider and/or that is a member of a compliance monitoring team of the healthcare provider. The user interface 640 may aggregate audit results for healthcare sites within the healthcare provider (e.g., particular types of healthcare sites, healthcare sites associated with a particular division of the healthcare provider, all healthcare sites managed or associated with the healthcare provider). The user interface 640 includes a risk count portion 654, a highest risk portion 648, a lowest risk portion 650, and an average score portion 652, which may be implemented similarly to the risk count portion 610, the highest risk portion 602, the lowest risk portion 604, and the average score portion 606, as discussed above.

The user interface 640 also includes an average score trendline portion 646 displaying trends for different types of audits (e.g., internal audits, manager audits, supervisor audits) over time (e.g., for each month over the last 12 months). The user interface 640 further includes an audit concerns section 644. The audit concerns section 644 may be configured to display the questions or categories of audits with the highest percentage of deficient status responses. The user interface 640 also includes a high-risk concerns section 642. The high-risk concerns section 642 may be configured to display questions or categories of audits with the highest percentage of deficient status responses, similar to the audit concerns section 644, but may only display concerns regarding high-risk questions or categories (e.g., questions or categories with risk values above a predetermined threshold).

Although not depicted, it should be understood that additional or alternative user interfaces to those discussed herein may be possible. For example, user interfaces may be generated and displayed to depict responses to individual audits and/or to highlight negative responses to particular audits or negative responses associated with particular healthcare sites. Furthermore, user interfaces may be displayed to further compare and/or subdivide risk scores according to different categories. For example, user interfaces may be generated and displayed that compare risk scores across multiple divisions or that compare risk scores across different auditors. In still further implementations, user interfaces may be displayed to compare and/or subdivide statuses of audits overall. For example, user interfaces may be generated and displayed that compare in progress, incomplete, not started, and/or past due audits by various categories (e.g., by division, by supervisor, by healthcare site, by employee). Additionally or alternatively, user interfaces may be displayed to further compare and/or analyze risk scores according to different categories (e.g., pharmacy risks, security risks) as defined within the audits.

Figure 7:
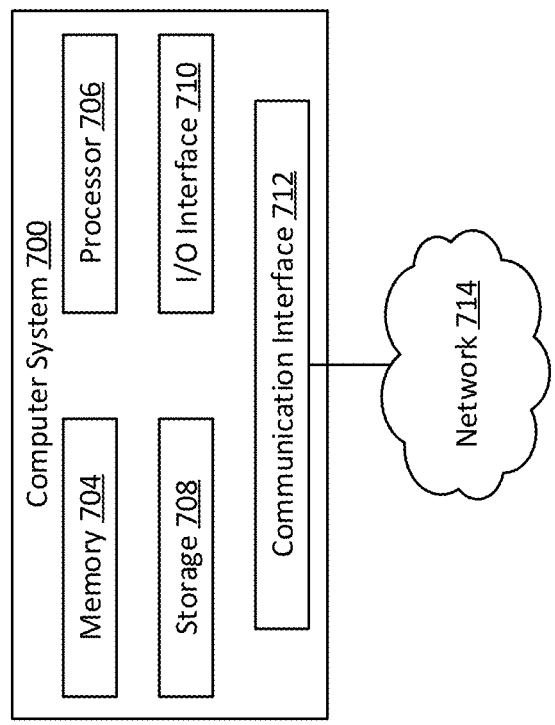
FIG. 7 illustrates a computer system according to an exemplary embodiment of the present disclosure.

FIG. 7 illustrates an example computer system 700 that may be utilized to implement one or more of the devices and/or components discussed herein, such as the computing system 102 and the audit database 104. In particular embodiments, one or more computer systems 700 perform one or more steps of one or more methods or calculations described or illustrated herein. In particular embodiments, one or more computer systems 700 provide the functionalities described or illustrated herein. In particular embodiments, software running on one or more computer systems 700 performs one or more steps of one or more methods described or illustrated herein or provides the functionalities described or illustrated herein. Particular embodiments include one or more portions of one or more computer systems 700. Herein, a reference to a computer system may encompass a computing device, and vice versa, where appropriate. Moreover, a reference to a computer system may encompass one or more computer systems, where appropriate.

This disclosure contemplates any suitable number of computer systems 700. This disclosure contemplates the computer system 700 taking any suitable physical form. As example and not by way of limitation, the computer system 700 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, the computer system 700 may include one or more computer systems 700; be unitary or distributed; span multiple locations; span multiple machines; span multiple data centers; or reside in a cloud, which may include one or more cloud components in one or more networks. Where appropriate, one or more computer systems 700 may perform without substantial spatial or temporal limitation one or more steps of one or more methods described or illustrated herein. As an example and not by way of limitation, one or more computer systems 700 may perform in real time or in batch mode one or more steps of one or more methods described or illustrated herein. One or more computer systems 700 may perform at different times or at different locations one or more steps of one or more methods described or illustrated herein, where appropriate.

In particular embodiments, computer system 700 includes a processor 706, memory 704, storage 708, an input/output (I/O) interface 710, and a communication interface 712. Although this disclosure describes and illustrates a particular computer system having a particular number of particular components in a particular arrangement, this disclosure contemplates any suitable computer system having any suitable number of any suitable components in any suitable arrangement.

In particular embodiments, the processor 706 includes hardware for executing instructions, such as those making up a computer program. As an example and not by way of limitation, to execute instructions, the processor 706 may retrieve (or fetch) the instructions from an internal register, an internal cache, memory 704, or storage 708; decode and execute the instructions; and then write one or more results to an internal register, internal cache, memory 704, or storage 708. In particular embodiments, the processor 706 may include one or more internal caches for data, instructions, or addresses. This disclosure contemplates the processor 706 including any suitable number of any suitable internal caches, where appropriate. As an example and not by way of limitation, the processor 706 may include one or more instruction caches, one or more data caches, and one or more translation lookaside buffers (TLBs). Instructions in the instruction caches may be copies of instructions in memory 704 or storage 708, and the instruction caches may speed up retrieval of those instructions by the processor 706. Data in the data caches may be copies of data in memory 704 or storage 708 that are to be operated on by computer instructions; the results of previous instructions executed by the processor 706 that are accessible to subsequent instructions or for writing to memory 704 or storage 708; or any other suitable data. The data caches may speed up read or write operations by the processor 706. The TLBs may speed up virtual-address translation for the processor 706. In particular embodiments, processor 706 may include one or more internal registers for data, instructions, or addresses. This disclosure contemplates the processor 706 including any suitable number of any suitable internal registers, where appropriate. Where appropriate, the processor 706 may include one or more arithmetic logic units (ALUs), be a multi-core processor, or include one or more processors 706. Although this disclosure describes and illustrates a particular processor, this disclosure contemplates any suitable processor.

In particular embodiments, the memory 704 includes main memory for storing instructions for the processor 706 to execute or data for processor 706 to operate on. As an example, and not by way of limitation, computer system 700 may load instructions from storage 708 or another source (such as another computer system 700) to the memory 704. The processor 706 may then load the instructions from the memory 704 to an internal register or internal cache. To execute the instructions, the processor 706 may retrieve the instructions from the internal register or internal cache and decode them. During or after execution of the instructions, the processor 706 may write one or more results (which may be intermediate or final results) to the internal register or internal cache. The processor 706 may then write one or more of those results to the memory 704. In particular embodiments, the processor 706 executes only instructions in one or more internal registers or internal caches or in memory 704 (as opposed to storage 708 or elsewhere) and operates only on data in one or more internal registers or internal caches or in memory 704 (as opposed to storage 708 or elsewhere). One or more memory buses (which may each include an address bus and a data bus) may couple the processor 706 to the memory 704. The bus may include one or more memory buses, as described in further detail below. In particular embodiments, one or more memory management units (MMUs) reside between the processor 706 and memory 704 and facilitate accesses to the memory 704 requested by the processor 706. In particular embodiments, the memory 704 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 704 may include one or more memories 704, where appropriate. Although this disclosure describes and illustrates particular memory implementations, this disclosure contemplates any suitable memory implementation.

In particular embodiments, the storage 708 includes mass storage for data or instructions. As an example and not by way of limitation, the storage 708 may include a hard disk drive (HDD), a floppy disk drive, flash memory, an optical disc, a magneto-optical disc, magnetic tape, or a Universal Serial Bus (USB) drive or a combination of two or more of these. The storage 708 may include removable or non-removable (or fixed) media, where appropriate. The storage 708 may be internal or external to computer system 700, where appropriate. In particular embodiments, the storage 708 is non-volatile, solid-state memory. In particular embodiments, the storage 708 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 708 taking any suitable physical form. The storage 708 may include one or more storage control units facilitating communication between processor 706 and storage 708, where appropriate. Where appropriate, the storage 708 may include one or more storages 708. Although this disclosure describes and illustrates particular storage, this disclosure contemplates any suitable storage.

In particular embodiments, the I/O Interface 710 includes hardware, software, or both, providing one or more interfaces for communication between computer system 700 and one or more I/O devices. The computer system 700 may include one or more of these I/O devices, where appropriate. One or more of these I/O devices may enable communication between a person (i.e., a user) and computer system 700. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. Where appropriate, the I/O Interface 710 may include one or more device or software drivers enabling processor 706 to drive one or more of these I/O devices. The I/O interface 710 may include one or more I/O interfaces 710, where appropriate. Although this disclosure describes and illustrates a particular I/O interface, this disclosure contemplates any suitable I/O interface or combination of I/O interfaces.

In particular embodiments, communication interface 712 includes hardware, software, or both providing one or more interfaces for communication (such as, for example, packet-based communication) between computer system 700 and one or more other computer systems 700 or one or more networks 714. As an example and not by way of limitation, communication interface 712 may include a network interface controller (NIC) or network adapter for communicating with an Ethernet or any other wire-based network or a wireless NIC (WNIC) or wireless adapter for communicating with a wireless network, such as a Wi-Fi network. This disclosure contemplates any suitable network 714 and any suitable communication interface 712 for the network 714. As an example and not by way of limitation, the network 714 may include one or more of an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 700 may communicate with a wireless PAN (WPAN) (such as, for example, a Bluetooth® WPAN), a WI-FI network, a WI-MAX network, a cellular telephone network (such as, for example, a Global System for Mobile Communications (GSM) network), or any other suitable wireless network or a combination of two or more of these. Computer system 700 may include any suitable communication interface 712 for any of these networks, where appropriate. Communication interface 712 may include one or more communication interfaces 712, where appropriate. Although this disclosure describes and illustrates a particular communication interface implementations, this disclosure contemplates any suitable communication interface implementation.

The computer system 702 may also include a bus. The bus may include hardware, software, or both and may communicatively couple the components of the computer system 700 to each other. As an example and not by way of limitation, the bus may include an Accelerated Graphics Port (AGP) or any other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local bus (VLB), or another suitable bus or a combination of two or more of these buses. The bus may include one or more buses, where appropriate. Although this disclosure describes and illustrates a particular bus, this disclosure contemplates any suitable bus or interconnect.

Herein, a computer-readable non-transitory storage medium or media may include one or more semiconductor-based or other types of integrated circuits (ICs) (e.g., field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, features, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

All of the disclosed methods and procedures described in this disclosure can be implemented using one or more computer programs or components. These components may be provided as a series of computer instructions on any conventional computer readable medium or machine readable medium, including volatile and non-volatile memory, such as RAM, ROM, flash memory, magnetic or optical disks, optical memory, or other storage media. The instructions may be provided as software or firmware, and may be implemented in whole or in part in hardware components such as ASICs, FPGAs, DSPs, or any other similar devices. The instructions may be configured to be executed by one or more processors, which when executing the series of computer instructions, performs or facilitates the performance of all or part of the disclosed methods and procedures.

It should be understood that various changes and modifications to the examples described here will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method comprising:
 (a) creating an audit that includes a plurality of questions;
 (b) using a machine learning model to determine a risk value for each of the plurality of questions, at least some of the questions corresponding to one or more policy requirements for healthcare sites, the machine learning model being trained using data regarding past audits for noncompliant healthcare sites and healthcare sites that experienced risk events, the machine learning model configured to assign relatively high risk values for questions that are more likely to be associated with a risk event or noncompliance of healthcare sites and questions that correspond to a greater number of policy requirements for healthcare sites;
 (c) receiving a plurality of responses associated with the audit of a healthcare site, the plurality of responses corresponding to the plurality of questions;
 (d) determining a status for each of the plurality of responses;
 (e) calculating a deficiency score for the healthcare site based on
  a first quantity of a subset of the plurality of responses indicating a deficient status for the healthcare site by summing risk values associated with the subset of the plurality of responses indicating the deficient status, and
  a second quantity of a subset of the plurality of responses indicating an improvement required status for the healthcare site by summing risk values associated with the subset of the plurality of responses indicating the improvement required status;
 (f) calculating a total score for the healthcare site based on a third quantity of the plurality of responses and a fourth quantity of a subset of the plurality of responses indicating an inapplicable status; and
 (g) calculating a risk score for the healthcare site based on the deficiency score and the total score.

2. The method of claim 1, wherein the deficiency score is calculated by applying a first weight to the first quantity and a second weight to the second quantity.

3. The method of claim 2, wherein the first weight is greater than the second weight.

4. The method of claim 3, wherein the first weight is at least two times larger than the second weight.

5. The method of claim 1, wherein the total score is calculated by subtracting the fourth quantity from the third quantity.

6. The method of claim 1, wherein the risk score is calculated by dividing the deficiency score by the total score.

7. The method of claim 6, wherein the risk score is calculated by subtracting an adjustment value from each of the deficiency score and the total score prior to dividing.

8. The method of claim 7, wherein the adjustment value is determined based on the total score and a configurable value.

9. The method of claim 1, wherein at least one of the third quantity is calculated by summing risk values associated with the plurality of responses, and the fourth quantity is calculated by summing risk values associated with the subset of the plurality of responses indicating the inapplicable status.

10. The method of claim 1, further comprising combining the risk score with a plurality of additional risk scores associated with additional healthcare sites to generate an aggregate risk score.

11. The method of claim 1, further comprising combining the risk score with at least one previous risk score associated with the healthcare site to generate a risk trend measurement for the healthcare site.

12. The method of claim 1, wherein (c) includes receiving a first plurality of responses associated with a regional audit of the healthcare site and a second plurality of responses associated with an on-site audit, and wherein (d) to (g) are performed twice to calculate a first risk score based on the first plurality of responses and a second risk score based on the second plurality of responses.

13. The method of claim 12, further comprising combining the first risk score and the second risk score to generate an overall risk score for the healthcare site.

14. The method of claim 1, wherein the deficient status includes any response indicating that a condition corresponding to the response does not comply with requirements for the condition.

15. The method of claim 1, wherein the improvement required status includes any response indicating that a condition corresponding to the response currently complies with requirements for the condition, but required correction before achieving compliance.

16. A system comprising:
a processor; and
a memory storing instructions which, when executed by the processor, cause the processor to:
(a) create an audit that includes a plurality of questions;
(b) use a machine learning model to determine a risk value for each of the plurality of questions, at least some of the questions corresponding to one or more policy requirements for healthcare sites, the machine learning model being trained using data regarding past audits for noncompliant healthcare sites and healthcare sites that experienced risk events, the machine learning model configured to assign relatively high risk values for questions that are more likely to be associated with a risk event or noncompliance of healthcare sites and questions that correspond to a greater number of policy requirements for healthcare sites;
(c) receive a plurality of responses associated with the audit of a healthcare site, the plurality of responses corresponding to the plurality of questions;
(d) determine a status for each of the plurality of responses;
(e) calculate a deficiency score for the healthcare site based on
a first quantity of a subset of the plurality of responses indicating a deficient status for the healthcare site by summing risk values associated with the subset of the plurality of responses indicating the deficient status, and
a second quantity of a subset of the plurality of responses indicating an improvement required status for the healthcare site by summing risk values associated with the subset of the plurality of responses indicating the improvement required status;
(f) calculate a total score for the healthcare site based on a third quantity of the plurality of responses and a fourth quantity of a subset of the plurality of responses indicating an inapplicable status; and
(g) calculate a risk score for the healthcare site based on the deficiency score and the total score.

17. The system of claim 16, wherein the deficiency score is calculated by performing at least one of (i) applying a first weight to the first quantity and a second weight to the second quantity, (ii) subtracting the fourth quantity from the third quantity, and (iii) dividing the deficiency score by the total score.

18. The system of claim 16, wherein at least one of the third quantity is calculated by summing risk values associated with the plurality of responses, and the fourth quantity is calculated by summing risk values associated with the subset of the plurality of responses indicating the inapplicable status.

19. The system of claim 16, wherein the memory stores further instructions which, when executed by the processor, cause the processor to perform at least one of (i) combining the risk score with a plurality of additional risk scores associated with additional healthcare sites to generate an aggregate risk score and (ii) combining the risk score with at least one previous risk score associated with the healthcare site to generate a risk trend measurement for the healthcare site.

20. The system of claim 16, wherein the deficient status includes any response indicating that a condition corresponding to the response does not comply with requirements for the condition, and wherein the improvement required status includes any response indicating that a condition corresponding to the response currently complies with requirements for the condition, but required correction before achieving compliance.

* * * * *